(12) United States Patent
Lee et al.

(10) Patent No.: US 9,358,239 B2
(45) Date of Patent: **\*Jun. 7, 2016**

(54) NISOD-LIKE COMPOUND AND ITS DERIVATIVES FOR SUPPRESSING ABNORMAL PROTEIN AGGREGATION, RECOVERING CELL VIABILITY, INCREASING MATURE NEURON NUMBER AND NEURITE OUTGROWTH LENGTH AND PROTECTING DOPAMINERGIC CELLS BY REDUCING OXIDATIVE STRESS OR REACTIVE OXYGEN SPECIES IN BRAIN TISSUES

(71) Applicant: National Taiwan Normal University, Taipei (TW)

(72) Inventors: Way-Zen Lee, Taipei (TW); Guey-Jen Lee, Taipei (TW); Hsiu-Mei Hsieh, Taipei (TW); Chien-Wei Chiang, Taipei (TW); Bin Huang, Taipei (TW); Yaw-Syan Fu, Taipei (TW); Yun-Ming Wang, Taipei (TW)

(73) Assignee: National Taiwan Normal University (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,968

(22) Filed: Jan. 26, 2015

(65) Prior Publication Data

US 2015/0209370 A1 Jul. 30, 2015

Related U.S. Application Data

(63) Continuation of application No. 13/492,657, filed on Jun. 8, 2012, now Pat. No. 8,642,763.

(60) Provisional application No. 61/931,789, filed on Jan. 27, 2014.

(51) Int. Cl.
*C07F 15/04* (2006.01)
*A61K 31/555* (2006.01)

(52) U.S. Cl.
CPC .................................... *A61K 31/555* (2013.01)

(58) Field of Classification Search
USPC .......................................... 514/188; 546/2, 6
See application file for complete search history.

(56) References Cited

U.S. PATENT DOCUMENTS 8,642,763 B2 2/2014 Lee

*Primary Examiner* — Charanjit Aulakh
(74) *Attorney, Agent, or Firm* — Bruce Stone LLP; Joseph Bruce

(57) ABSTRACT

The accumulation of abnormal proteins in neurodegenerative disorders is considered to induce oxidative stress and lead to cell death. Thus suppression of abnormal protein aggregation and reducing oxidative stress or reactive oxygen species (ROS) are expected to inhibit a wide range of harmful downstream events, providing an observation for identifying the potential prevention and treatment of neurodegenerative disorders comprising spinocerebellar ataxia (SCA), Alzheimer's disease (AD) or Parkinson's disease (PD). In the present invention, there are several cell and animal experiment models for SCA, AD and PD established, and NiSOD-like compounds were applied to these experiment models. The results have demonstrated how NiSOD-like compounds are likely to work in suppressing abnormal protein aggregation, recovering cell viability, increasing mature neuron number and neurite outgrowth length and protecting dopaminergic cells by reducing oxidative stress or reactive oxygen species in brain tissues.

10 Claims, 29 Drawing Sheets
(7 of 29 Drawing Sheet(s) Filed in Color)

NISOD-LIKE COMPOUND AND ITS DERIVATIVES FOR SUPPRESSING ABNORMAL PROTEIN AGGREGATION, RECOVERING CELL VIABILITY, INCREASING MATURE NEURON NUMBER AND NEURITE OUTGROWTH LENGTH AND PROTECTING DOPAMINERGIC CELLS BY REDUCING OXIDATIVE STRESS OR REACTIVE OXYGEN SPECIES IN BRAIN TISSUES

CROSS-REFERENCE

This application claims the benefits of U.S. Provisional Application No. 61/931,789 filed on Jan. 27, 2014 and claims priority to U.S. Pat. No. 8,642,763 published on Feb. 4, 2014, all of which are incorporated herein by reference.

BACKGROUND OF THE INVENTION

1. Field of the Invention

The present invention relates to utilize NiSOD-like compound and derivatives thereof as a pharmaceutical composition. More specifically, NiSOD-like compound and derivatives thereof are used for suppressing abnormal protein aggregation, recovering cell viability, increasing mature neuron number and neurite outgrowth length and protecting dopaminergic cells by reducing oxidative stress or reactive oxygen species in brain tissues.

2. Description of the Prior Art

As the elderly population of the world continues to increase, the prevalence of neurodegenerative disorders, such as spinocerebellar ataxia (SCA), Alzheimer's disease (AD) and Parkinson's disease (PD), has been increasing at a disconcerting rate. Despite tremendous progress that has made in neurodegenerative disorders research in the past few decades, there is still no effective treatment for such diseases.

Neurodegeneration is an umbrella term for the progressive loss of structure or function of neurons, including death of neurons. As research progresses, many similarities appear that are related these diseases to one another on a cellular level. Discovering these similarities offers hope for therapeutic advances that could ameliorate many diseases simultaneously. There are many parallels between different neurodegenerative disorders including atypical protein assemblies as well as induced cell death; moreover, with age, the risk of DNA mutation increases, as well as the risk of cell damage induced by oxidative stress.

Although SCA, AD and PD manifest with different clinical features, the disease processes at the cellular level appear to be similar.

In SCA disease, the expansions of CAG repeats in the disease genes result in long polyglutamine (polyQ) tracts in the respective proteins. The accumulation of intranuclear and cytoplasmic misfolded polyQ proteins is thought to induce oxidative stress and lead to cell death. Patients with SCA find that their ability to use the affected parts of the body becomes progressively more difficult and less exact.

AD has been categorized to be a protein misfolding disease, caused by accumulation of abnormally folded A-beta and tau proteins in the brain, which leads to progressive loss of memory. A-beta protein is made up of small peptides, 39-43 amino acids in length, called beta-amyloid (also written as Aβ oligomer). Aβ oligomer is a fragment from a larger protein called amyloid precursor protein (APP), a transmembrane protein that penetrates through the neuron's membrane. APP is critical to neuron growth, survival and post-injury repair.

PD is a neurodegenerative movement disorder. In most cases it occurs as a sporadic type of disease, but there are also rare familial forms. Pathologically Parkinson's disease is characterized by loss of dopaminergic neurons in the compact part of substantia nigra. As a part of the neurodegenerative process protein aggregates will accumulate as Lewy bodies in dopaminergic neurons. In PD, research on protein misfolding and aggregation has taken center stage following the association of alpha-synuclein gene mutations with familial forms of the disease.

The above protein aggregation leads to the increase of oxidative stress which has been implicated as a factor for the initiation and progression of neurodegenerative disorders. Thus, suppression of the protein aggregation and reduction of oxidative stress in the neurodegenerative disorders are expected to inhibit a wide range of harmful downstream events and further provide an observation for identifying the potential prevention and treatment of neurodegenerative disorders.

SUMMARY OF THE INVENTION

To achieve suppression of the protein aggregation and by reduction of oxidative stress or reactive oxygen species in brain tissues in accordance with the purpose of the invention as embodied and broadly described herein, the present invention provides NiSOD-like compound and derivatives thereof for suppressing abnormal protein aggregation, recovering cell viability, increasing mature neuron number and neurite outgrowth length and protecting dopaminergic cells by reducing oxidative stress or reactive oxygen species in brain tissues in SCA, AD or PD.

The NiSOD-like compound or its derivatives implemented in the present invention has a five-coordinate structural formula (I):

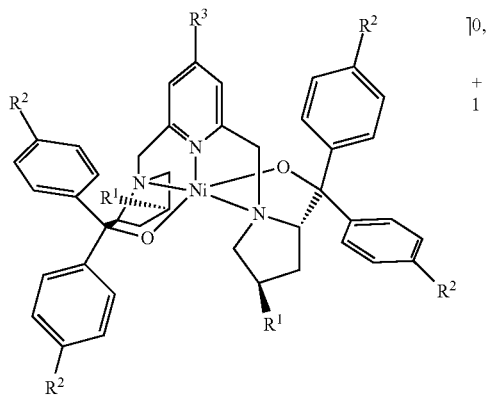

wherein $R^1$ denotes H or -A-R'; wherein A denotes O or N; wherein R' is H, an alkoxy group, an amino acid group, or a polymeric group; wherein the polymeric group is a polyethyleneoxy group, a polydimethylsiloxane group, or polyurethane; wherein $R^2$ is H or a para-substituent of a phenyl ring, the para-substituent of the phenyl ring is selected from a group consisting of alkyl groups, alkoxy groups, silane groups, amino groups, alkyl amino groups, and a hydroxyl group; wherein $R^3$ is H or a para-substituent of a pyridine ring, the para-substituent of the pyridine ring is selected from a group consisting of amino groups, alkyl amino groups, siloxane amino groups, and siloxane amino groups which attach to a $Fe_3O_4/SiO_2$ magnetic nanoparticle; and wherein Ni is a nickel(II) or nickel(III) ion.

Besides, the NiSOD-like compound or its derivatives can be a six-coordinate derivative having a structural formula (II):

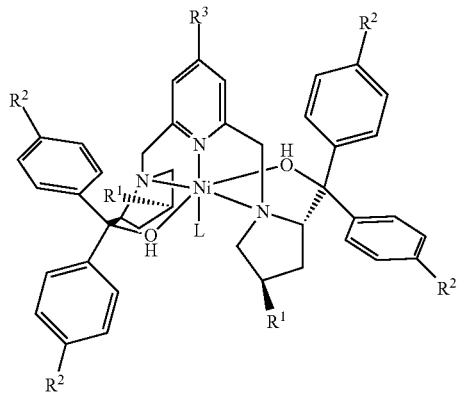

(II)

wherein $R^1$, $R^2$ and $R^3$ are defined in the above paragraph, and L is acetonitrile, water or tert-butyl isocyanate. The six-coordinate derivative comprises WCt003, WCt006 or WCt021.

The WCt003 has the following structural formula:

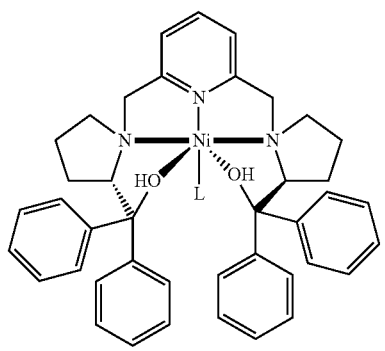

(WCt003)

The WCt006 has the following structural formula:

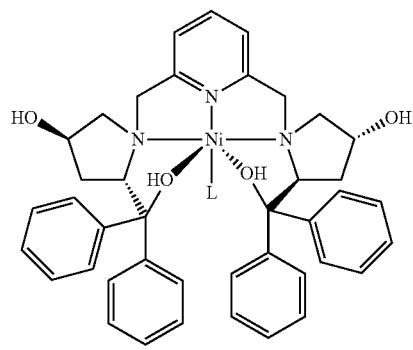

(WCt006)

The WCt021 has the following structural formula:

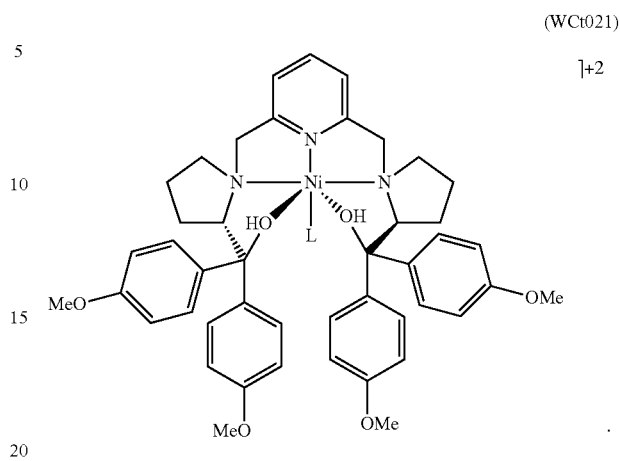

(WCt021)

The NiSOD-like compound or its derivatives can suppress abnormal protein aggregation, recovering cell viability, increasing mature neuron number and neurite outgrowth length and protecting dopaminergic cells by reducing oxidative stress or reactive oxygen species (ROS).

A detailed description of further features in the present invention is given below so that a person skilled in the art is allowed to understand and carry out the technical contents of the present invention, and can readily comprehend the objectives and advantages of the present invention after reviewing the contents disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings are included to provide a further understanding of the invention, and are incorporated in and constitute a part of this specification. The drawings illustrate embodiments of the invention and, together with the description, serve to explain the features and advantages of the invention. In the drawings.

DESCRIPTION OF THE PREFERRED EMBODIMENTS

Figure 1:
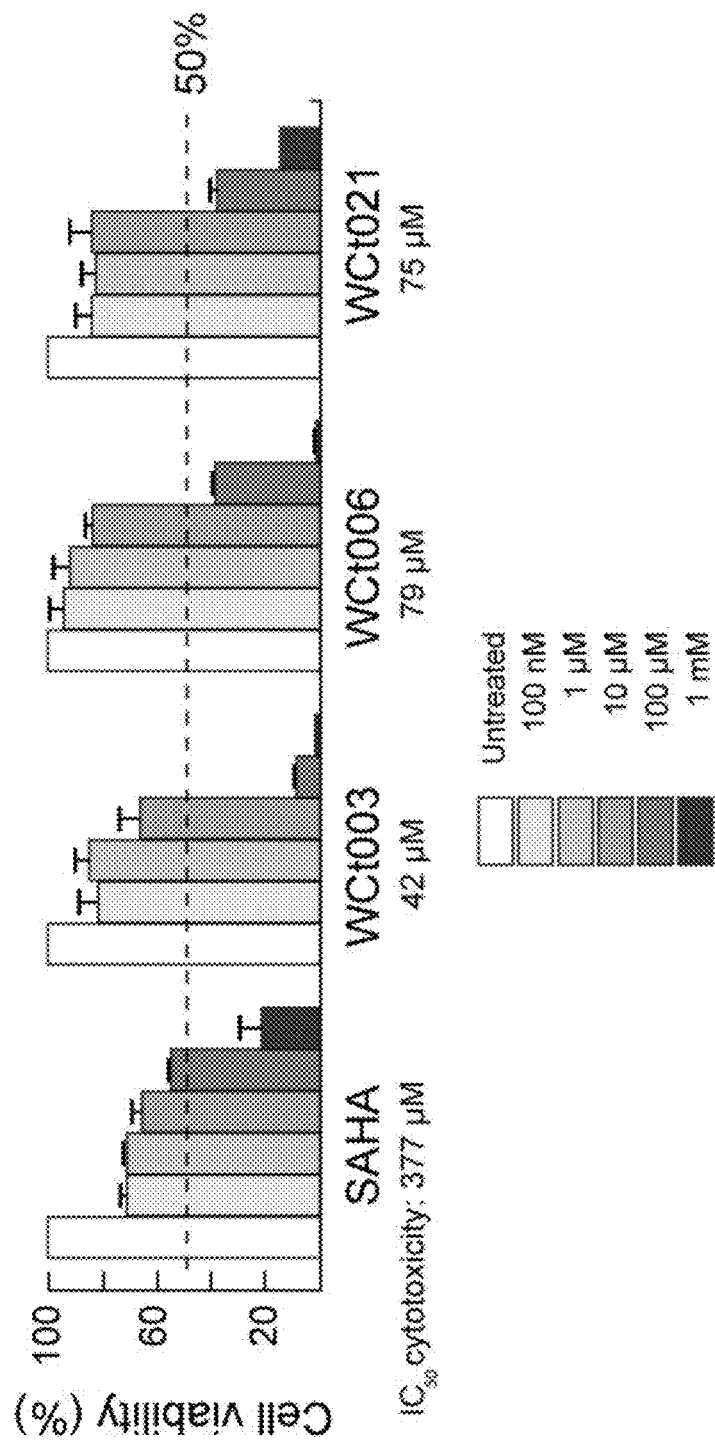
FIG. 1 is a bar chart illustrating the cell cytotoxicity of SAHA, WCt003, WCt006 and WCt021 against 293 cells using MTT viability assay according to an embodiment of the present invention.

The present invention provides a pharmaceutical composition which comprises a NiSOD-like compound or derivatives thereof with an effective dose for suppressing abnormal protein aggregation, recovering cell viability, increasing mature neuron number and neurite outgrowth length and protecting dopaminergic cells by reducing oxidative stress or reactive oxygen species in brain tissues. The effective dose may be a prophylactically effective amount as prophylaxis.

There are several cell and animal experiment models provided below for demonstrating the capabilities of suppressing abnormal protein aggregation, recovering cell viability, increasing mature neuron number and neurite outgrowth length and protecting dopaminergic cells by reducing oxidative stress or reactive oxygen species of the NiSOD-like compound or derivatives thereof. Furthermore, the results were confirmed with brain slice culture of spinocerebellar ataxia 17 (SCA17) transgenic mice and Alzheimer's disease (AD) mice, brain tissues immunostaining of Parkinson's disease (PD) mice, and SCA17 transgenic, AD and PD mice.

I. Preparation of Nisod-Like Compound and Derivatives Thereof

The NiSOD-like compound or derivatives thereof mentioned and the producing method thereof are disclosed in U.S. Pat. No. 8,642,763, which is incorporated herein by reference. In U.S. Pat. No. 8,642,763, a nickel complex or derivatives thereof is used for mimicking the active site of the nickel-containing superoxide dismutase (NiSOD), and is considered as a NiSOD-like compound. The present invention provides a novel use of the NiSOD-like compound for suppressing abnormal protein aggregation, recovering cell viability, increasing mature neuron number and neurite outgrowth length and protecting dopaminergic cells by reducing oxidative stress or reactive oxygen species in brain tissues in neurodegenerative disorders comprising spinocerebellar ataxia, Alzheimer's disease or Parkinson's disease.

The preparation method of the NiSOD-like compound is to sequentially react [2,6-bis(((S)-2-(diphenylhydroxymethyl)-1-pyrrolidinyl)methyl)pyri-dine] ($H_2BDPP$) or the derivative of $H_2BDPP$ with NaH and $[Ni(CH_3CN)_6](ClO_4)_2$ or only with $[Ni(CH_3CN)_6](ClO_4)_2$. For example,

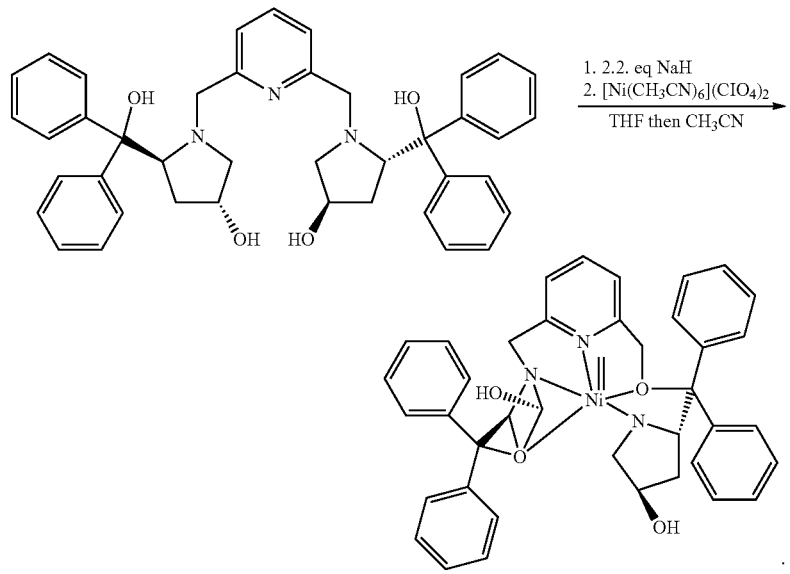

This example adopted a reaction precursor OH-BDPP wherein the pyrrolidinyl group was attached with a hydroxyl group. According to the preparation method, let 0.128 g (0.2 mmol) OH-BDPP sequentially react with 0.012 g (0.5 mmol) NaH and 0.101 g (0.2 mmol) $[Ni(CH_3CN)_6](ClO_4)_2$ at ambient temperature for 2 hours to obtain a five-coordinate nickel (II) complex, Ni—OH-BDPP. Two derivatives, a five-coordinate nickel(III) complex, $[Ni—OH-BDPP]PF_6$, and a six-coordinate nickel(II) complex, Ni—OH—$H_2$BDPP (WCt006), were obtained from further fabrication of the abovementioned five-coordinate nickel(II) complex, Ni—OH-BDPP. With the proposed preparation method, WCt003 and WCt021 have been also prepared for the following experiments.

In the present invention, Student's t-test is used, and all P values are two-tailed, with vales of P<0.05 considered significant. For each set of values, data are expressed as the means±standard deviation (SD), and significance is expressed as * or #.

II. Experiments of Spinocerebellar Ataxia (SCA)

In SCA, the expansions of CAG repeats in the disease genes result in long polyglutamine (polyQ) tracts in the respective proteins. The accumulation of intranuclear and cytoplasmic misfolded polyQ proteins is thought to induce oxidative stress and lead to cell death. In the cell and animal experiment models, synthetic compounds WCt003, WCt006 and WCt021 were applied to demonstrate how WCt003, WCt006 and WCt021 are likely to work in protein aggregation suppression and oxidative stress reduction.

A. Cell Culture and Cytotoxicity of NiSOD-Like Compounds Assay

Human embryonic kidney HEK-293 cells (ATCC No. CRL-1573) were cultivated in Dulbecco's modified Eagle's medium (DMEM) containing 10% fetal bovine serum (FBS). HEK-293 cells were cultivated at 37° C. incubator containing 5% $CO_2$ and cell proliferation was measured based upon the reduction of the tetrazolium salt, 3,[4,5-dimethylthiazol-2-yL]-2,5-diphenyl-tetrazolium bromide (MTT). MTT viability assay was used for accessing the cytotoxicity of WCt003, WCt006 and WCt021 and comparing the cytotoxicity of WCt003, WCt006 and WCt021 with that of SAHA (suberoylanilide hydroxamic acid, Cayman Chemical) which is a well-known HDAC (Histone Deacetylase) inhibitor for reducing SDS (Sodium dodecyl sulfate)-insoluble polyQ aggregate.

HEK-293 cells were plated into 48-well ($5\times10^4$/well) dishes, grown for 20 hours and treated with different concentrations of SAHA, WCt003, WCt006 and WCt021 (0 nM, 100 nM, 1 μM, 10 μM, 100 μM, and 1 mM) respectively. After one day, 20 μL MTT (5 mg/ml in PBS, Sigma) was added to cells and incubated for 2 hours. The absorbance of the purple formazan dye was measured at 570 nm by a Bio-Tek μQuant Universal Microplate Spectrophotometer. For each set of values, data are expressed as the means±standard deviation (SD).

As MTT viability assays were performed with human embryonic kidney 293 cells after treatment with the tested NiSOD-like compounds for one day, the $IC_{50}$ was calculated using the interpolation method. Refer to FIG. 1. SAHA, WCt003, WCt006 and WCt021 respectively had an $IC_{50}$ of 377 μM, 42 μM, 79 μM and 75 μM. To normalize, the relative viability in untreated cells is set as 100% viability. The horizontal line represents 50% viability. FIG. 1 demonstrates that WCt003, WCt006 and WCt021 are less cytotoxic than SAHA in the concentration between 100 nM to 10 μM.

B. Construction of 293 Cells Expressing ATXN3/$Q_{75}$ Aggregates

Figure 2:
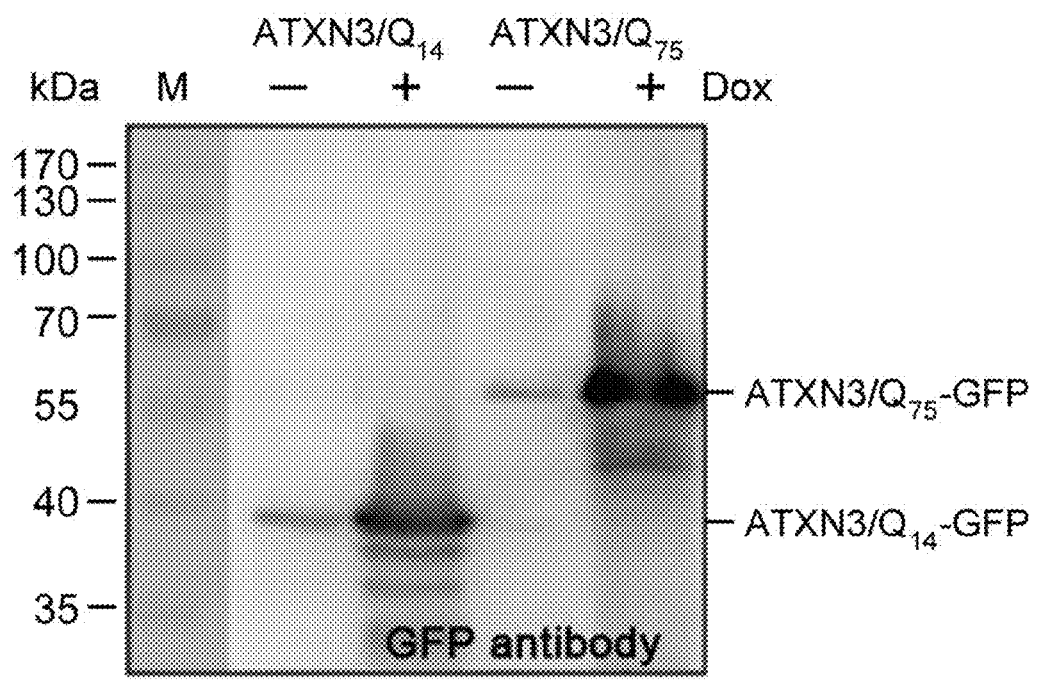
FIG. 2 shows an image of Western blot analysis of ATXN3/$Q_{14\text{-}75}$-GFP protein expression using GFP antibody after two days induction (+Dox) according to an embodiment of the present invention.
Figure 3A:
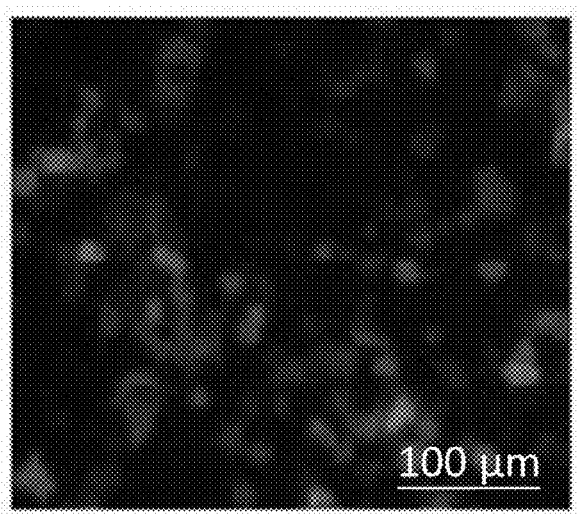
FIG. 3A shows fluorescence microscopy images of ATXN3/$Q_{14}$-GFP expression after six days induction according to an embodiment of the present invention.
Figure 3B:
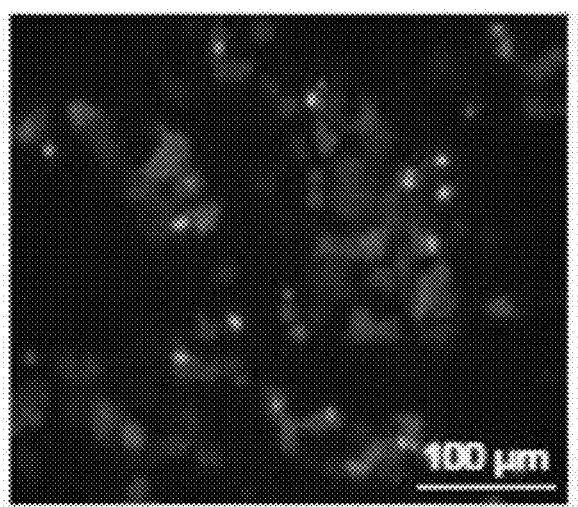
FIG. 3B shows fluorescence microscopy images of ATXN3/$Q_{75}$-GFP expression after six days induction according to an embodiment of the present invention.

For therapies toward the polyQ diseases, we aimed to screen compounds potentially inhibiting polyQ aggregation. As removal of the N-terminal ATXN3 was required for ATXN3 aggregation, GFP-tagged ATXN3/$Q_{14-75}$ C-terminal fragment was cloned to establish Flp-In 293 cells with inducible ATXN3/$Q_{14-75}$-GFP expression. Refer to FIG. 2. The GFP antibody detected 40~57 kDa ATXN3/$Q_{14-75}$-GFP proteins in doxycycline (+Dox) induced ATXN3 cells. Refer to FIGS. 3A and 3B. While the expressed ATXN3/$Q_{14}$ was primarily diffused, the expressed ATXN3/$Q_{75}$-GFP formed aggregates. For high content aggregation analysis, these ATXN3/$Q_{75}$ cells were seeded onto 96-well plate, treated with tested compounds WCt003, WCt006 and WCt021 for 8 hours, and doxycycline was added to induce ATXN3/$Q_{75}$-GFP expression for 6 days. Oxaliplatin (5 μM, Sigma) was added for aggregate accumulation through inhibition of DNA synthesis. Then cells were stained with Hochest 33342 (0.1 μg/ml, Sigma) and aggregation percentage was assessed by high-content analysis (HCA) system, with excitation/emission wavelengths at 482/536 (GFP).

Figure 4:
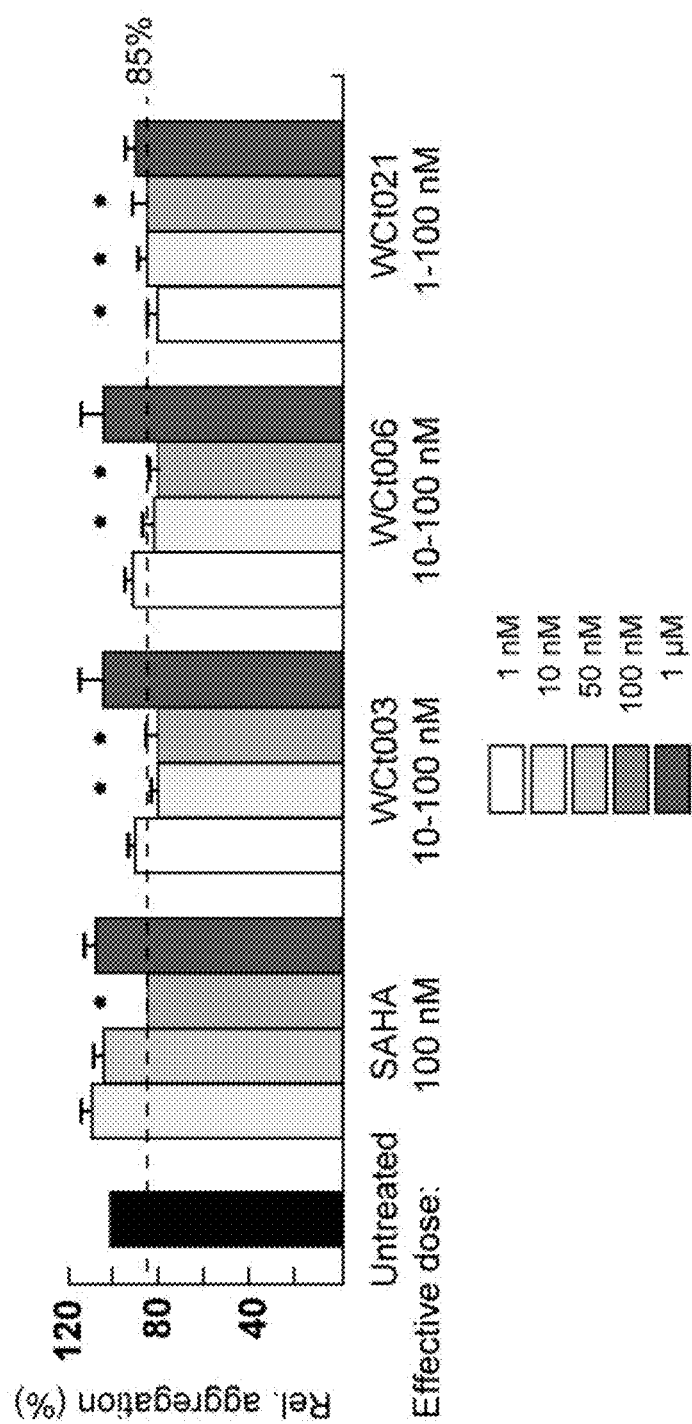
FIG. 4 is a bar chart illustrating the aggregation analysis of ATXN3/$Q_{75}$-GFP cells untreated or treated with SAHA, WCt003, WCt006 and WCt021 according to an embodiment of the present invention.

C. NiSOD-Like Compounds Treatment Reduces ATXN3/$Q_{75}$ Aggregation on 293 Cell Model Refer to FIG. 4. Cells expressing ATXN3/$Q_{75}$ were examined with tested compounds WCt003, WCt006 and WCt021. As a positive control, HDAC inhibitor SAHA reduced the ATXN3/$Q_{75}$ aggregation to 85% at 100 nM as compared to untreated cells. WCt003 and WCt006 reduced the ATXN3/$Q_{75}$ aggregation to 80% to 84% at 10 nM and 100 nM, and WCt021 reduced the ATXN3/$Q_{75}$ aggregation to 80% to 84% at 1 nM to 100 nM. The tested compounds display aggregation-inhibitory potential.

D. NiSOD-Like Compounds Treatment Reduces ROS Production on 293 Cell Model

Figure 5A:
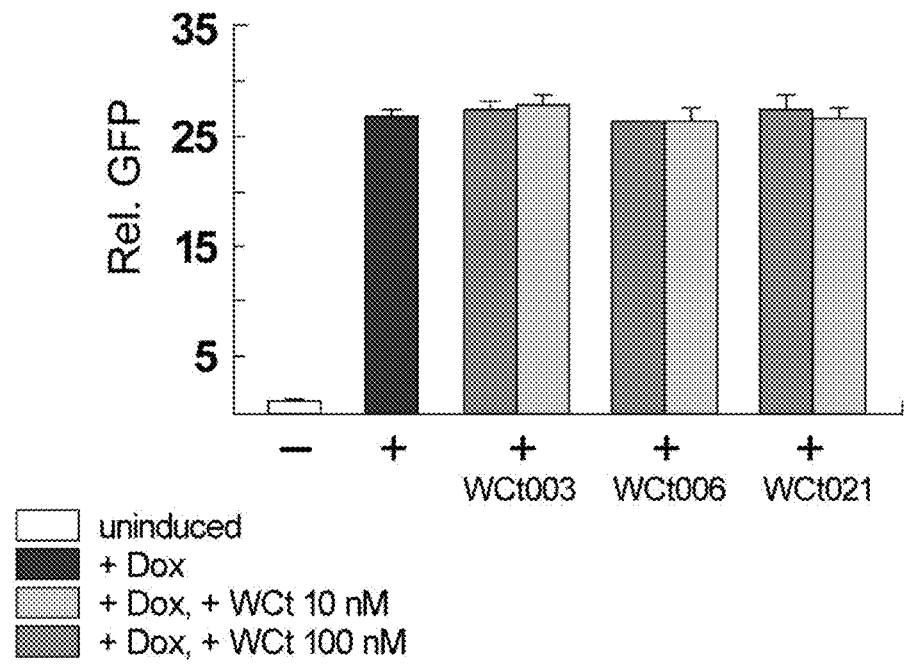
FIG. 5A is a bar chart illustrating the relative GFP level in 293 ATXN3/$Q_{75}$-GFP cells after treating with WCt003, WCt006 and WCt021 for 8 hours and inducing ATXN3/$Q_{75}$-GFP expression for 6 days according to an embodiment of the present invention.
Figure 5B:
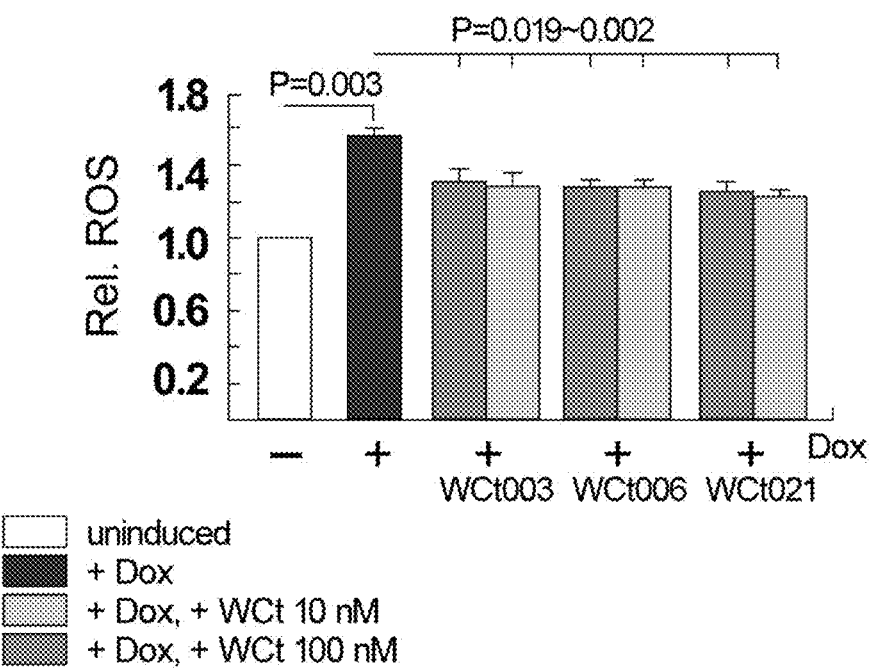
FIG. 5B is a bar chart illustrating the relative ROS level in 293 ATXN3/$Q_{75}$-GFP cells after treating with WCt003, WCt006 and WCt021 for 8 hours and inducing ATXN3/$Q_{75}$-GFP expression for 6 days according to an embodiment of the present invention.

Production of reactive oxygen species (ROS) is a particularly destructive aspect of oxidative stress; such species include free radicals, peroxides and superoxide. To evaluate whether NiSOD-like compounds reduced ROS formation in 293 ATXN3/$Q_{75}$ cells, the cellular production of ROS was measured by using a red fluorescent probe from Molecular Probes. After treating with WCt003, WCt006 and WCt021 in concentration of 10 nM to 100 nM for 8 hours and inducing ATXN3/$Q_{75}$-GFP expression for 6 days, the red fluorescent probe exhibited bright fluorescence upon oxidation by ROS. With absorption/emission maxima at 644/665 nm, the fluorescence of the red fluorescent probe can be detected using fluorescence microscopy and analyzed by HCA system. Refer to FIG. 5A. The similar induced green fluorescence protein GFP is 26.3 to 27.8 folds. Refer to FIG. 5B. Induced expression of ATXN3/$Q_{75}$ for 6 days significantly increases the ROS production (156%, P=0.003). Pretreatment of WCt003, WCt006 and WCt021 in concentration of 10 nM to 100 nM significantly ameliorated oxidative stress induced by ATXN3/$Q_{75}$ from 156% to 123%~130% (P=0.019~0.002).

Figure 6A:
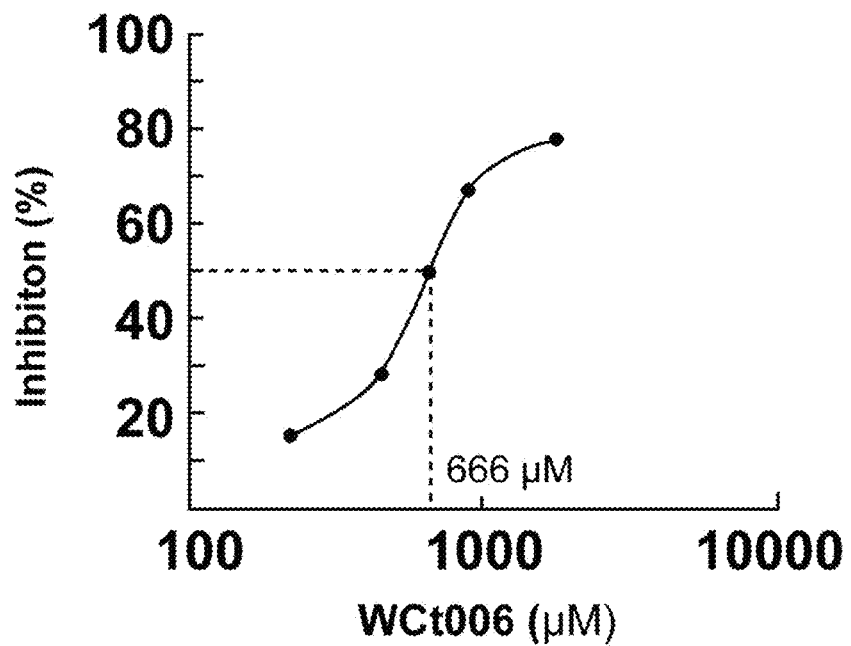
FIG. 6A is a diagram illustrating SOD-like activity of WCt006 according to an embodiment of the present invention.
Figure 6B:
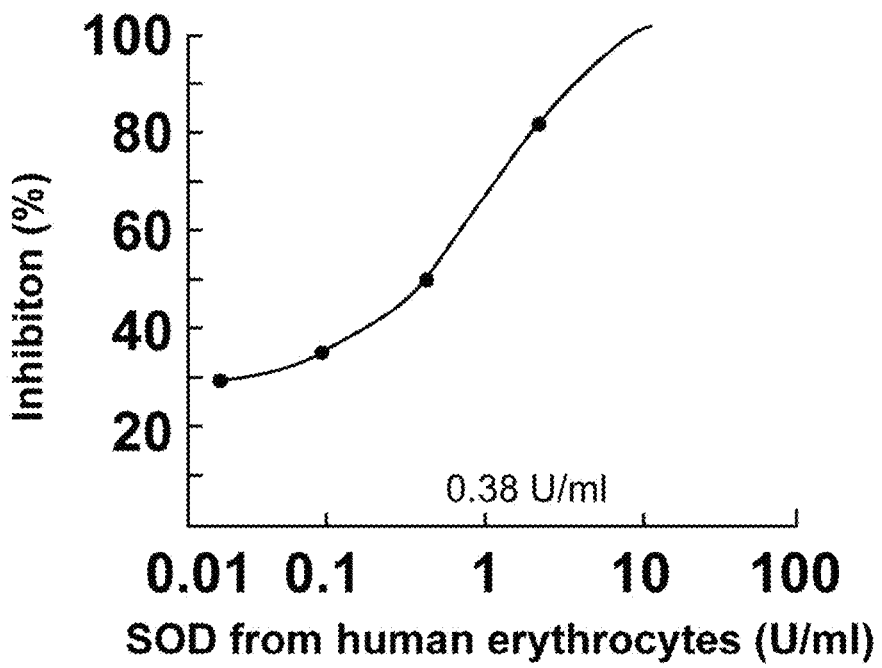
FIG. 6B is a diagram illustrating activity of SOD enzyme from human erythrocytes according to an embodiment of the present invention.
Figure 6C:
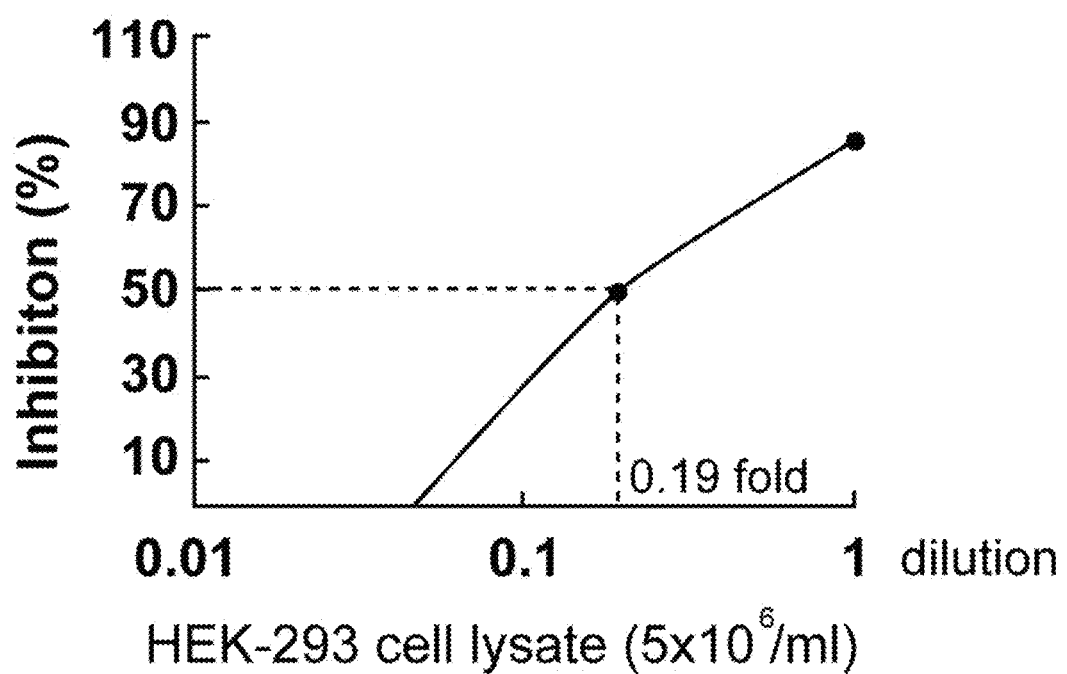
FIG. 6C is a diagram illustrating SOD-like activity of HEK-293 cell lysate according to an embodiment of the present invention.

E. Superoxide Dismutase (SOD)-Like and DPPH Free Radical Scavenging Activities of NiSOD-Like Compounds For SOD activity, SOD enzyme from human erythrocytes (Sigma, catalog number 59636) and HEK-293 cell lysate ($5\times10^6$/ml) were used as comparison. The SOD Assay Kit-WST from Dojindo was used to determine SOD activity. The assay utilizes WST-1 [2-(4-iodophenyl)-3-(4-nitrophenyl)-5-(2,4)-disulfophenyl-2H-tetrazolium, monosodium salt] that produces a water-soluble formazan dye upon reduction with the superoxide anion. The rate of the reduction of WST-1 with $O_2^-$ was linearly related to the xanthine oxidase (XO) activity, and this reduction was inhibited by SOD. Therefore, the $IC_{50}$ (50% inhibition activity of SOD or SOD-like materials) can be determined by the colorimetric method. Refer to FIG. 6A. $IC_{50}$ of WCt006 is 666 μM. Refer to FIG. 6B. $IC_{50}$ of SOD enzyme from human erythrocytes is 0.38 U/ml. Refer to FIG. 6C. $IC_{50}$ of HEK-293 cell lysate is 0.19 dilution fold.

Figure 7:
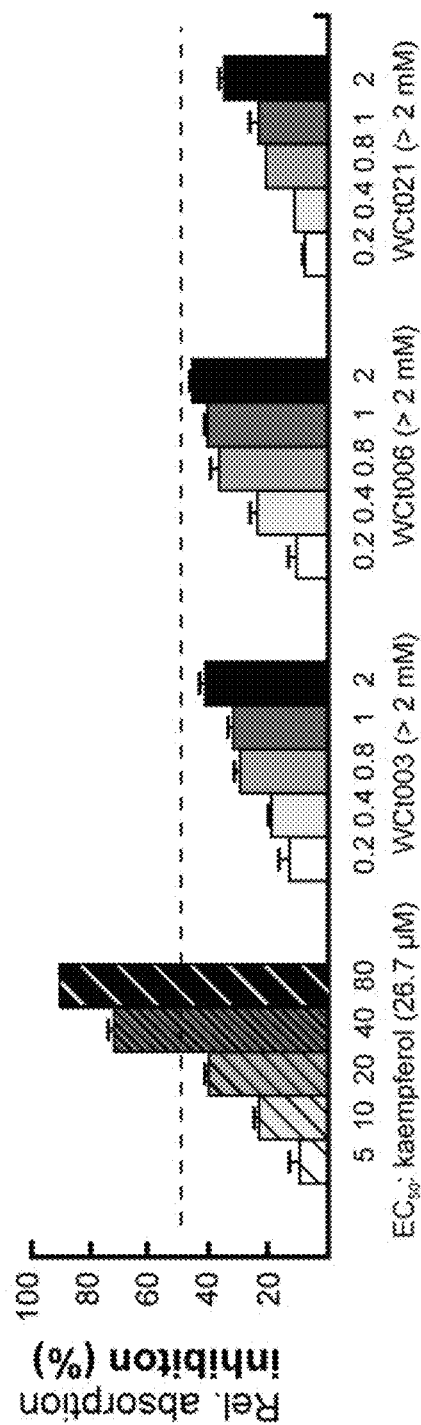
FIG. 7 is a diagram illustrating DPPH free radical scavenging activity of Kaempferol, WCt003, WCt006 and WCt021 according to an embodiment of the present invention.

For DPPH (1,1-diphenyl-2-picryl hydrazyl) scavenging activity, the odd electron in the stable DPPH free radical gives a strong absorption maximum at 517 nm and is purple in color. The DPPH assay measured scavenging ability of the antioxidants towards the stable radical. The free radical DPPH was reduced when it reacted with antioxidants and results in decrease in absorbance at 517 nm. The degree of discoloration indicated the scavenging potential of the antioxidant compounds. Refer to FIG. 7. The present invention had tested the NiSOD-like compounds (WCt003, WCt006, and WCt021) with excellent DPPH scavenging activity, especially WCt021 having better DPPH scavenging activity. $EC_{50}$ of kaempferol (a natural flavonol with antioxidant activity) and NiSOD-like compounds are 26.7 μM and >2 mM, respectively.

F. Organotypic Cerebellar Slice Culture and Immunofluorescent Staining

Figure 8A:
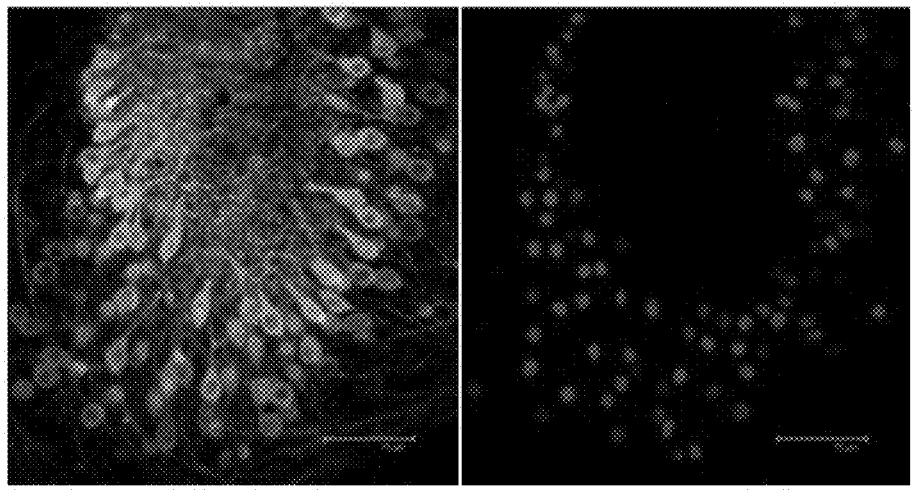
FIG. 8A shows immunostaining microscopic images of slice cultures with untreated vehicle according to an embodiment of the present invention.
Figure 8B:
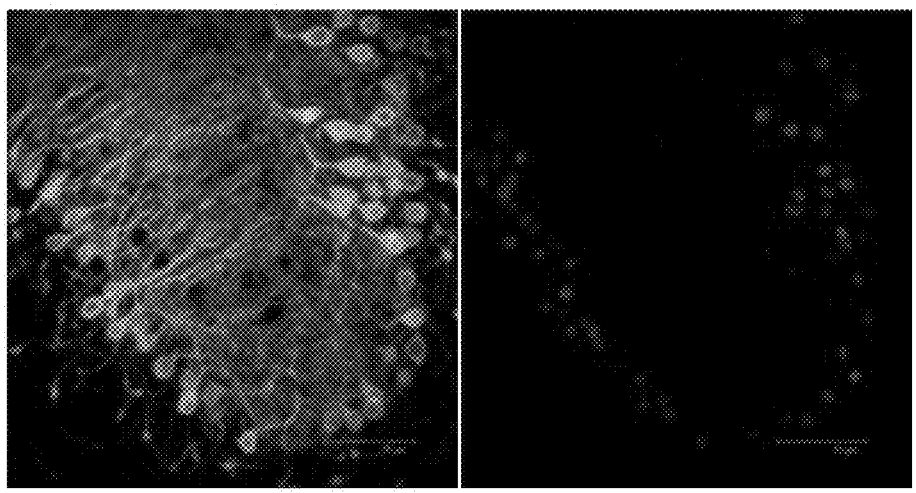
FIG. 8B shows immunostaining microscopic images of slice cultures with WCt003 treated according to an embodiment of the present invention.
Figure 8C:
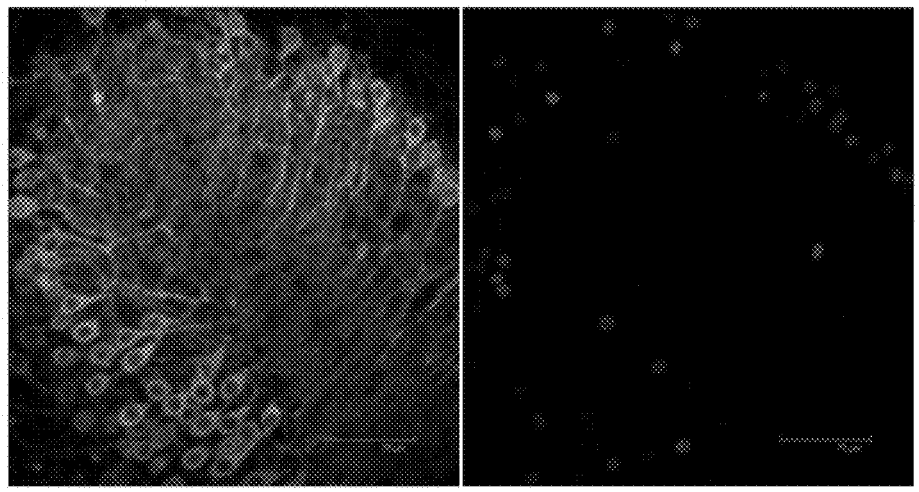
FIG. 8C shows immunostaining microscopic images of slice cultures with WCt006 treated according to an embodiment of the present invention.
Figure 8D:
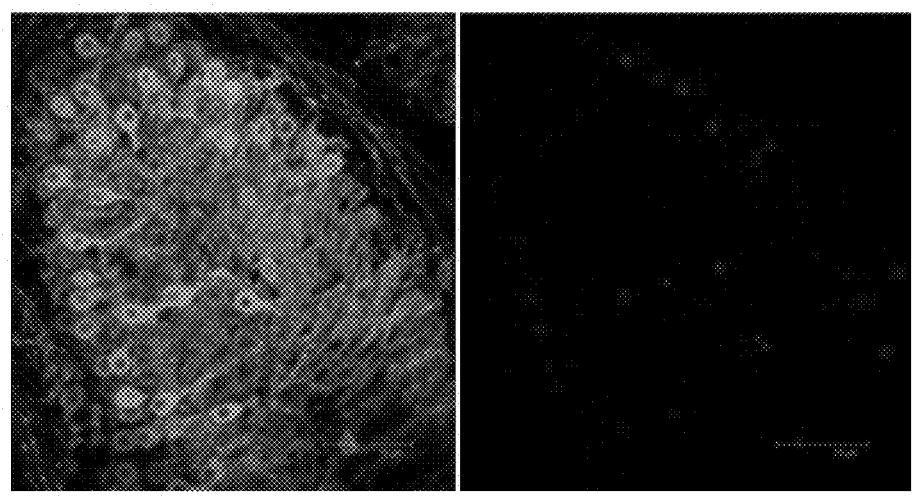
FIG. 8D shows immunostaining microscopic images of slice cultures with WCt021 treated according to an embodiment of the present invention.
Figure 8E:
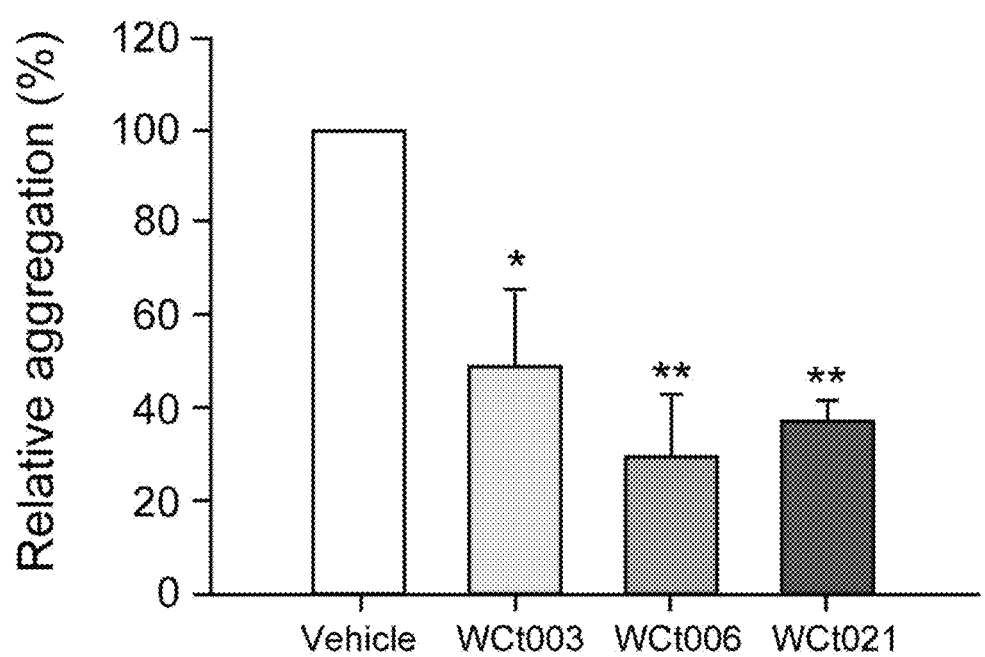
FIG. 8E is a bar chart illustrating relative aggregation in SCA17 mouse cerebellar slice culture with untreated vehicle, WCt003 treated, WCt006 treated and WCt021 treated according to an embodiment of the present invention.

The cerebellar slices were prepared from postnatal day 7 SCA17 transgenic (TG) mice and cultured on 0.4 μm pore size culture plate inserts in six-well plates (Millipore). NiSOD-like compounds, WCt003, WCt006 and WCt021, were applied in concentration of 10 nM to 20 nM to the slices at day 2. After culture for 7 days, slices were immunostained with primary antibodies IP3R-1 for Purkinje cells and 1TBP18 for TBP aggregation, fluorescence-conjugated secondary antibodies and DAPI for nuclei. The staining results were observed by confocal microscope. Three independent experiments were performed and differences between groups were evaluated by Student's t-test. Refer to FIGS. 8A, 8B, 8C and 8D. The representative immunostaining microscopic images of slice cultures are shown. In FIG. 8A, immunostaining microscopic images show slice cultures of Purkinje cells and TBP protein aggregation with untreated vehicle. In FIG. 8B, immunostaining microscopic images show slice cultures of Purkinje cells and TBP protein aggregation with WCt003 treated. In FIG. 8C, immunostaining microscopic images show slice cultures of Purkinje cells and TBP protein aggregation with WCt006 treated. In FIG. 8D, immunostaining microscopic images show slice cultures of Purkinje cells and TBP protein aggregation with WCt021 treated. Refer to FIG. 8E. The quantitative results of immunostaining are shown, and NiSOD-like compounds treatment significantly reduces the mutant TBP protein aggregation. In FIG. 8E, * indicates $p<0.05$; ** indicates $p<0.01$.

G. Mouse Rotarod Performance During NiSOD-Like Compounds Treatment

Figure 9:
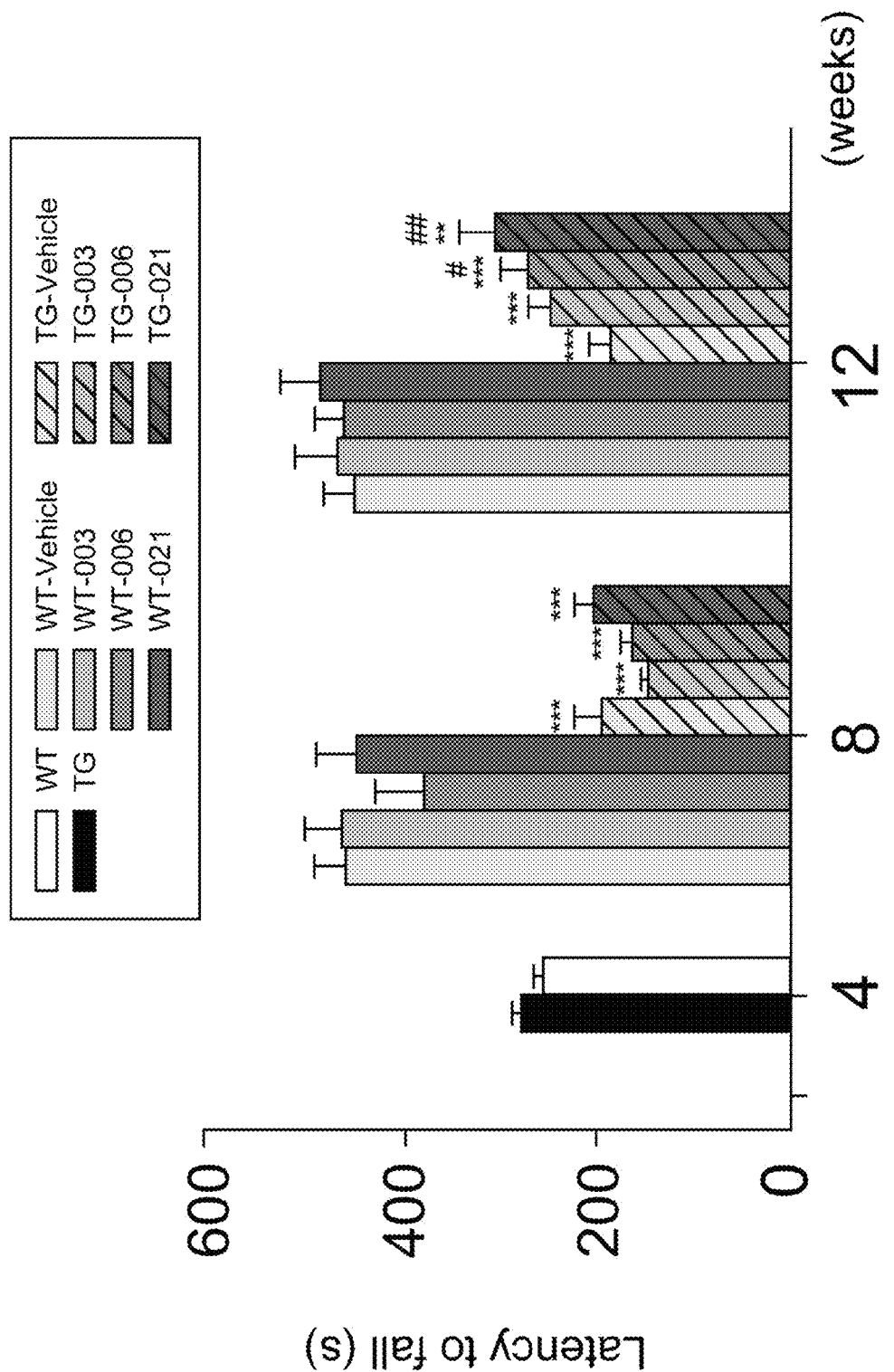
FIG. 9 is a bar chart illustrating mouse rotarod performance during NiSOD-like compounds treatment in comparison between SCA17 transgenic mice and their wild-type littermates according to an embodiment of the present invention.

Both SCA17 transgenic (TG) mice (N=60) and their wild-type (WT) littermates (N=60) were divided into 4 groups (N=15/per group). Mouse rotarod performance was evaluated at 4 weeks old prior to NiSOD-like compounds treatment. NiSOD-like compounds, WCt003, WCt006 and WCt021 (2 mg/kg, respectively), or vehicle (DMSO) were intraperitoneal injected into the mice every day for 10 weeks. Rotarod performance was conducted every month. Refer to FIG. 9. WCt006 and WCt021 significantly improve the rotarod performance of SCA17 TG mice. In FIG. 9, # indicates $p<0.05$;  and ## indicate $p<0.01$; * indicates $p<0.001$, wherein the * is TG vs. WT, and the # is TG/WCt vs. TG/vehicle.

H. NiSOD-Like Compounds Treatment Reduces Oxidative Response of SCA17 Mice

Figure 10:
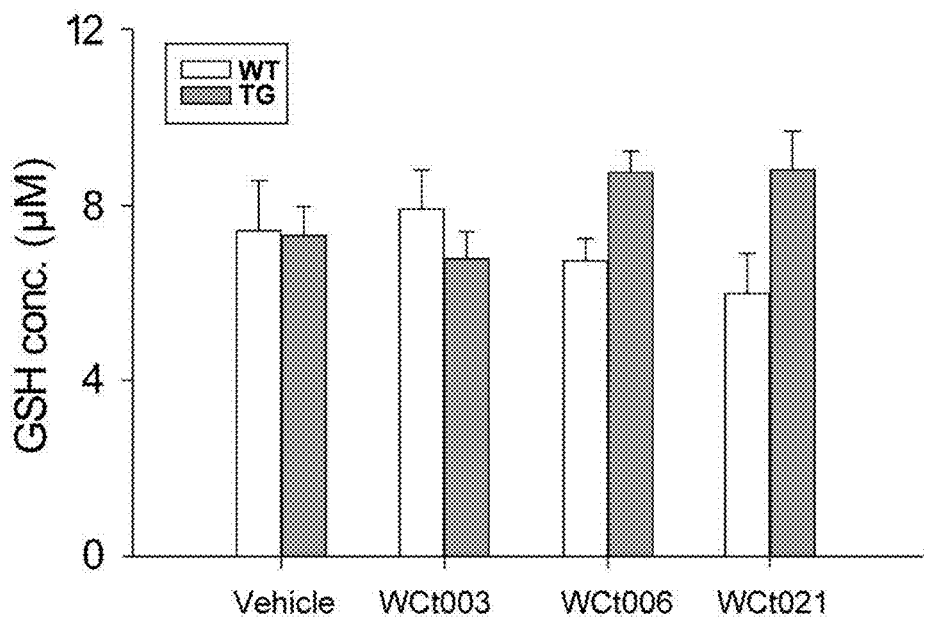
FIG. 10 is a bar chart illustrating the increase of glutathione level in SCA17 transgenic mice after NiSOD-like compounds treatment according to an embodiment of the present invention.

Glutathione (GSH) plays a critical role in the cellular defense against oxidative stress in mammalian cells. Plasma was collected from the peripheral blood of 14-week old mice and the GSH level was measured by GSH assay kit (Cayman Chemical, Ann Arbor, Mich., USA). Refer to FIG. 10. The quantitative result shows no significant difference in the plasma GSH level between WT and TG mice. However, WCt006 and WCt021 treatment can slightly increase the GSH level in TG mice.

Figure 11A:
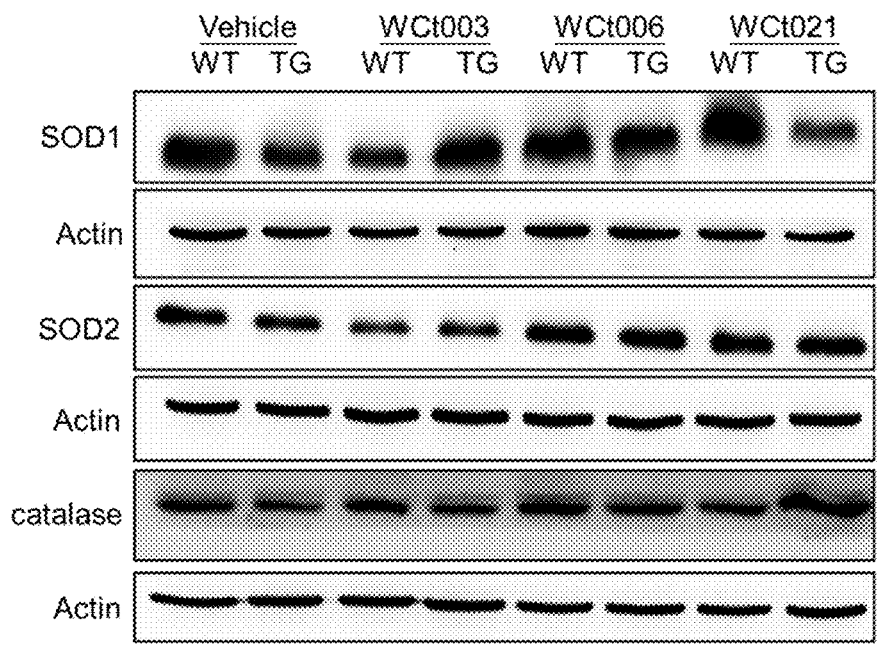
FIG. 11A shows an image of Western blot analysis of anti-oxidative enzymes SOD1, SOD2 and catalase according to an embodiment of the present invention.

Refer to FIG. 11A. Protein was extracted from the cerebellum of 14-week old mice and used to conduct the Western blot analysis of anti-oxidative enzymes SOD1, SOD2 and catalase.

Figure 11B:
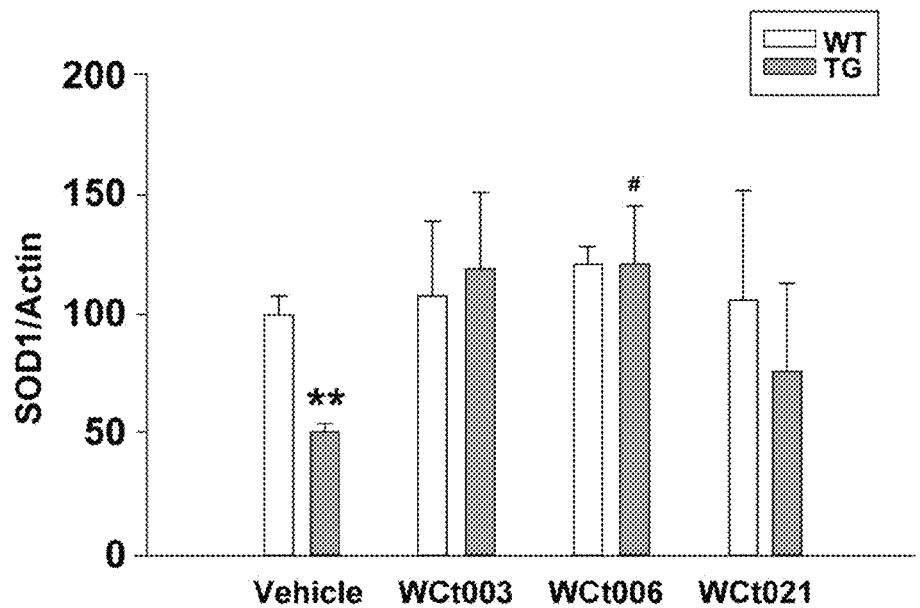
FIG. 11B is a bar chart illustrating the increase of SOD1 level in SCA17 transgenic mice after NiSOD-like compounds treatment according to an embodiment of the present invention.
Figure 11C:
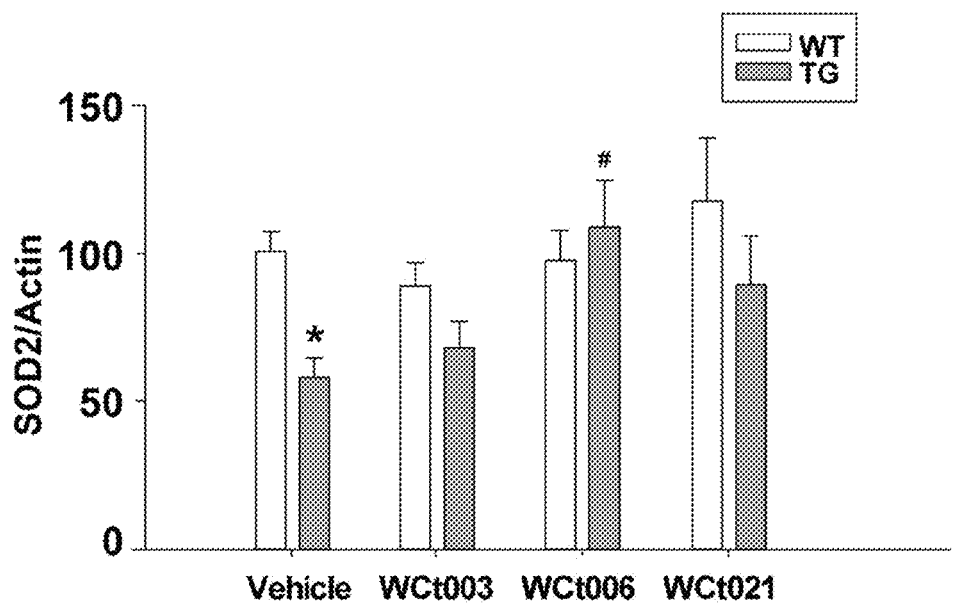
FIG. 11C is a bar chart illustrating the increase of SOD2 level in SCA17 transgenic mice after NiSOD-like compounds treatment according to an embodiment of the present invention.
Figure 11D:
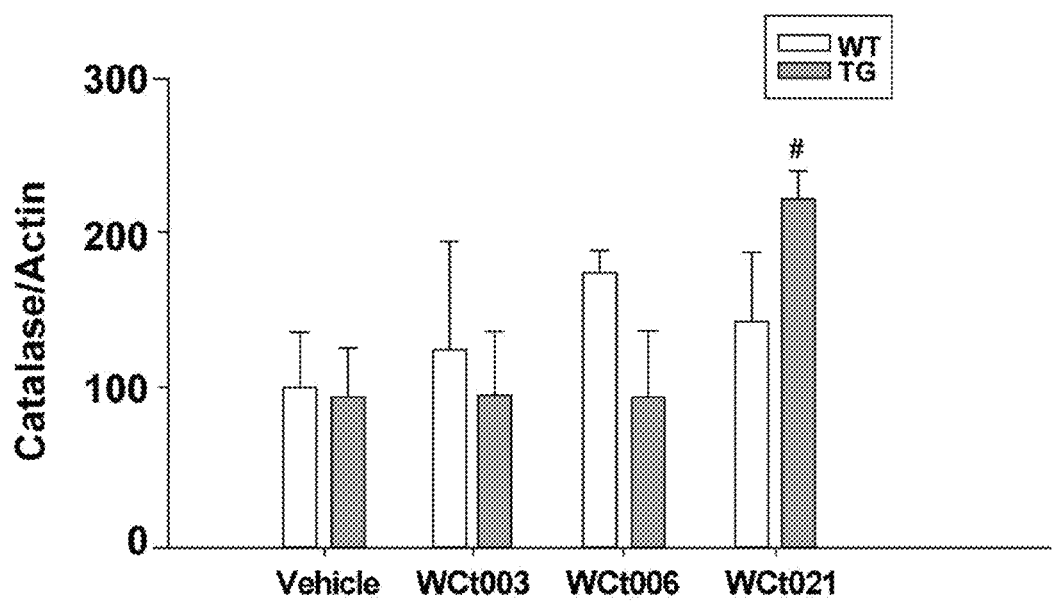
FIG. 11D is a bar chart illustrating the increase of catalase level in SCA17 transgenic mice after NiSOD-like compounds treatment according to an embodiment of the present invention.

Refer to FIGS. 11B and 11C. The quantitative result of Western blot show the SOD1 and SOD2 are significantly reduced in SCA17 TG mice, which suggests significant oxidative stress occurred in SCA17 mouse cerebellum. Treatment with WCt006 significantly increased the levels of SOD1 and SOD2. Refer to FIG. 11D. In addition, although there is no difference in catalase level between WT and TG mice, WCt021 can significantly elevated the catalase in TG mice. In FIGS. 11B, 11C and 11D, * and # indicate $p<0.05$; ** indicates $p<0.01$, wherein the * is TG vs. WT, and the # is TG/WCt vs. TG/vehicle.

I. NiSOD-Like Compounds Treatment Reduces Mutant TBP Protein Aggregation

Figure 12A:
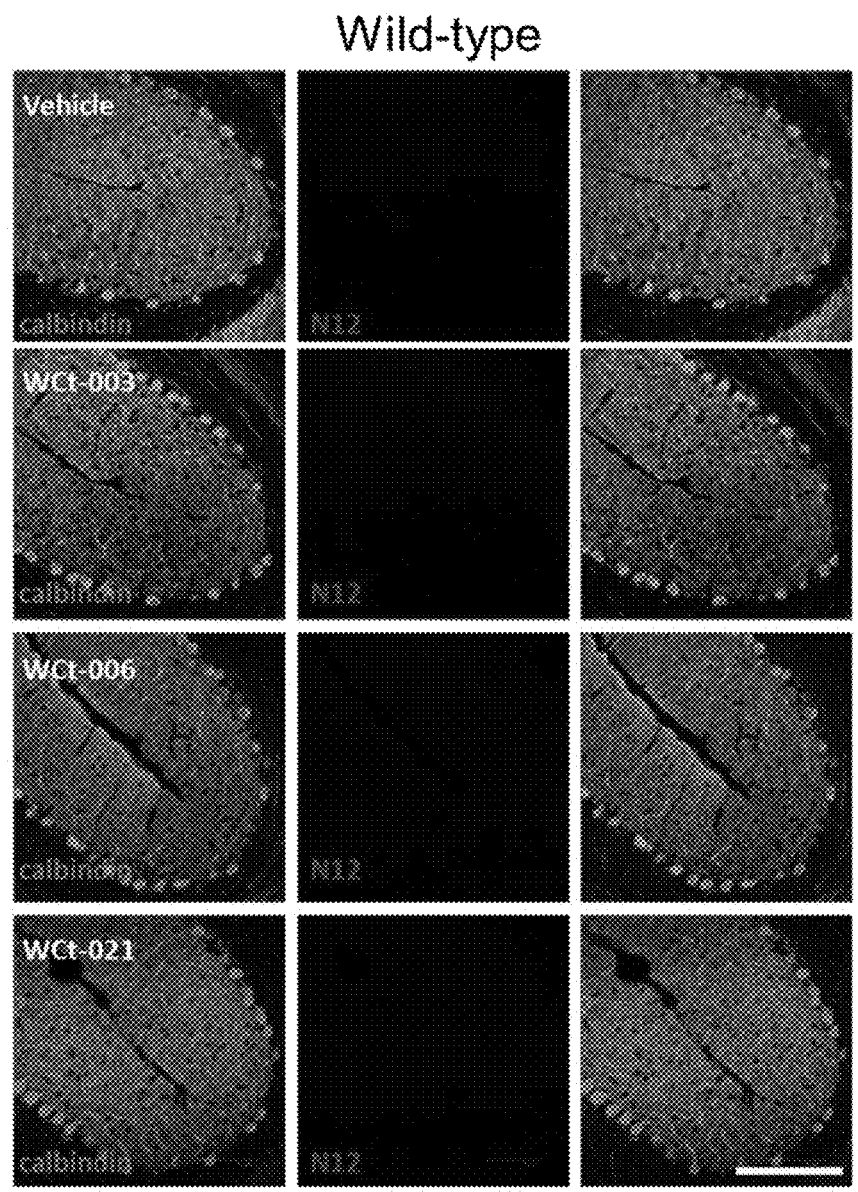
FIG. 12A shows immunofluorescent staining images of Purkinje neurons and TBP protein aggregation in wild-type mice according to an embodiment of the present invention.
Figure 12B:
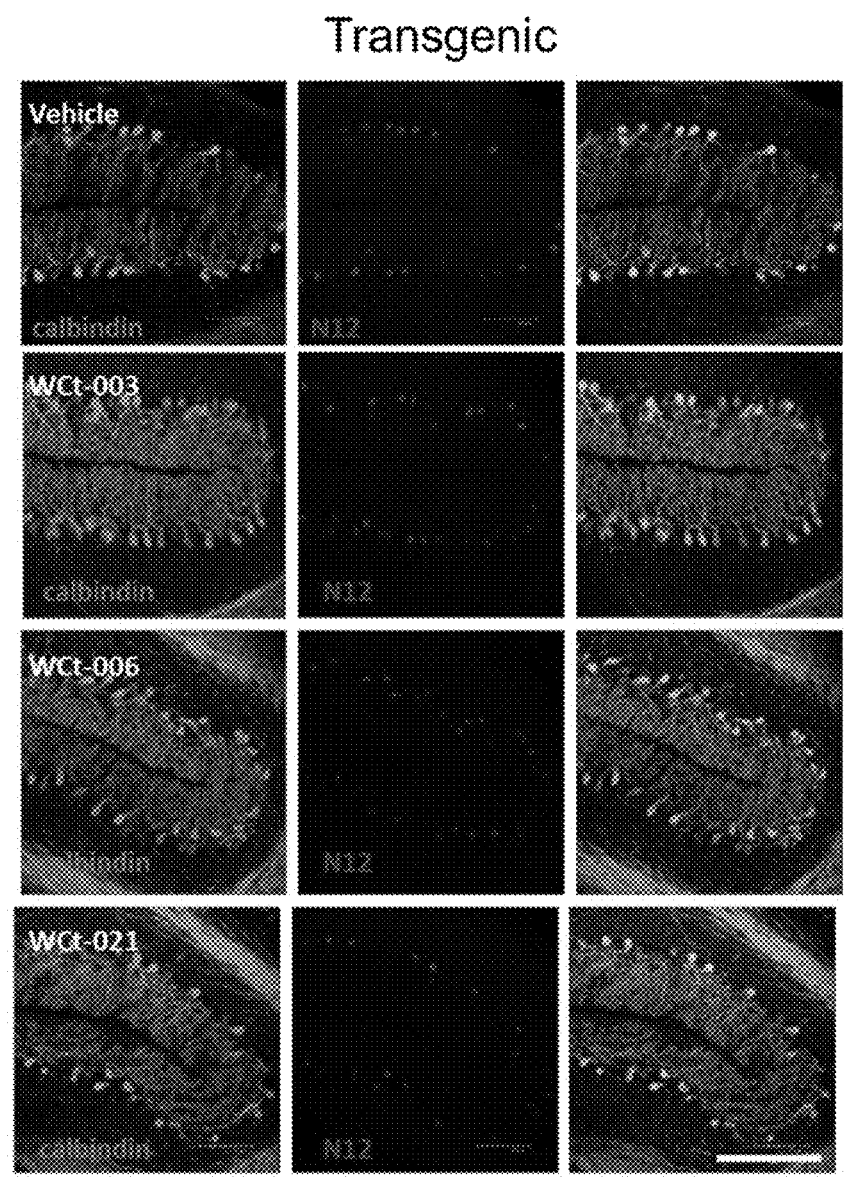
FIG. 12B shows immunofluorescent staining images of Purkinje neurons and TBP protein aggregation in transgenic SCA17 mice according to an embodiment of the present invention.
Figure 12C:
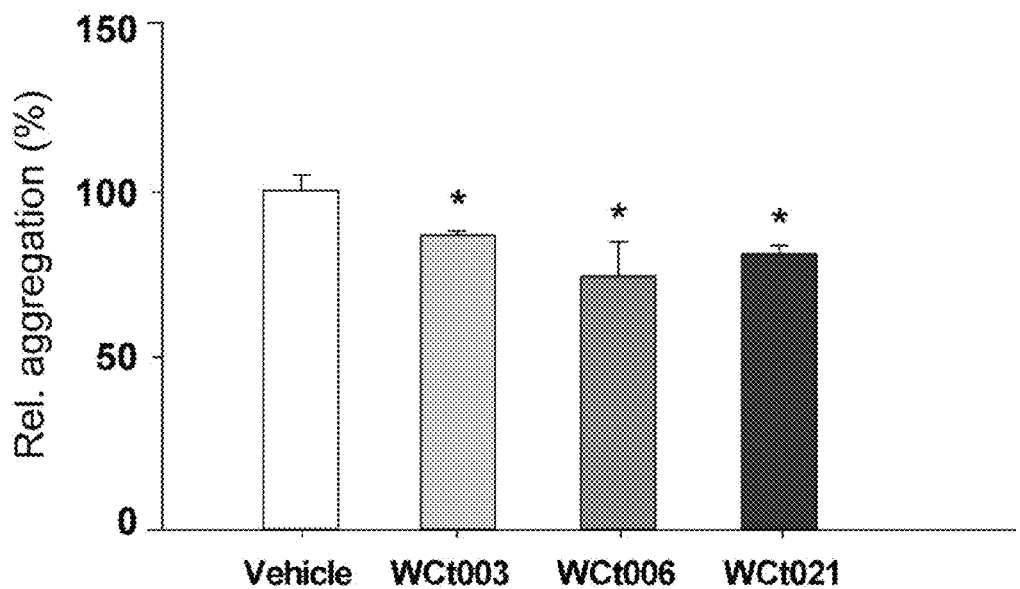
FIG. 12C is a bar chart illustrating the reduction of TBP protein aggregation in Purkinje neurons of SCA17 mouse cerebellum after NiSOD-like compounds treatment according to an embodiment of the present invention.

Refer to FIGS. 12A and 12B. The cerebella were isolated from 14-week-old SCA17 mice for immunofluorescent staining with calbindin (Purkinje neurons) and N12 (TBP protein aggregation). In FIG. 12A, immunofluorescent staining images show Purkinje neurons and TBP protein aggregation in wild-type mice. In FIG. 12B, immunofluorescent staining images show Purkinje neurons and TBP protein aggregation in SCA17 transgenic mice. Refer to FIG. 12C. The quantitative result of immunofluorescent staining shows all the three WCt compounds can significantly reduce the mutant TBP protein aggregation in Purkinje neurons of SCA17 mouse cerebellum. In FIG. 12C, * indicates $p<0.05$.

Figure 13A:
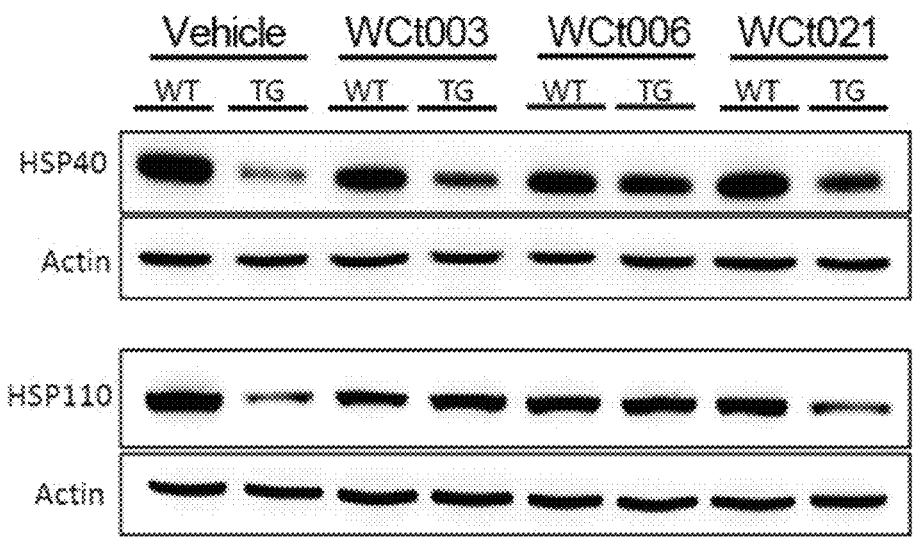
FIG. 13A shows an image of Western blot analysis of chaperones HSP40 and HSP110 according to an embodiment of the present invention.
Figure 13B:
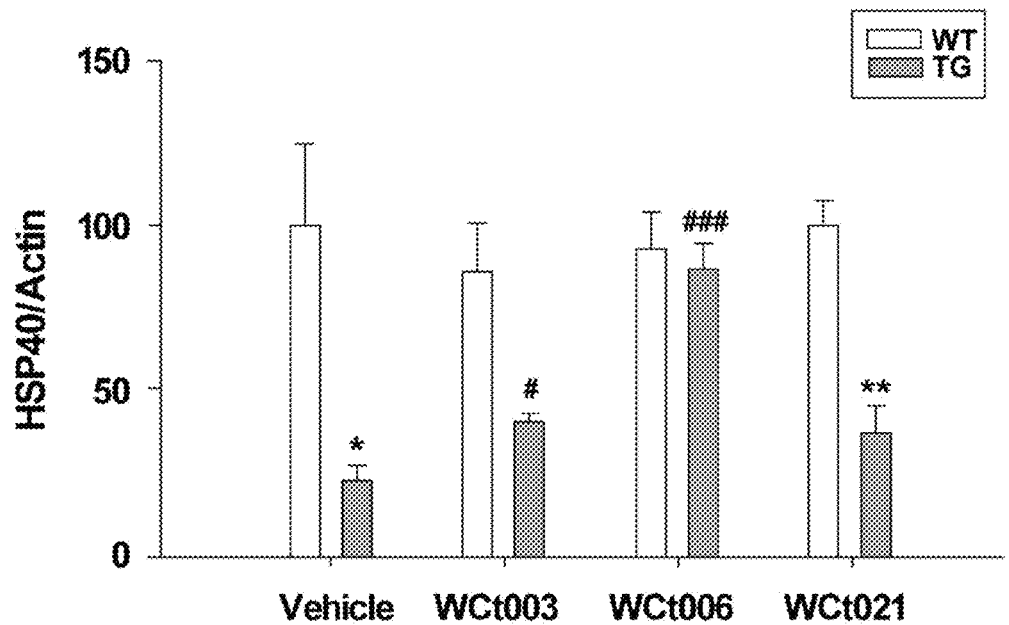
FIG. 13B is a bar chart illustrating the increase of chaperone HSP40 expression level after NiSOD-like compounds treatment according to an embodiment of the present invention.
Figure 13C:
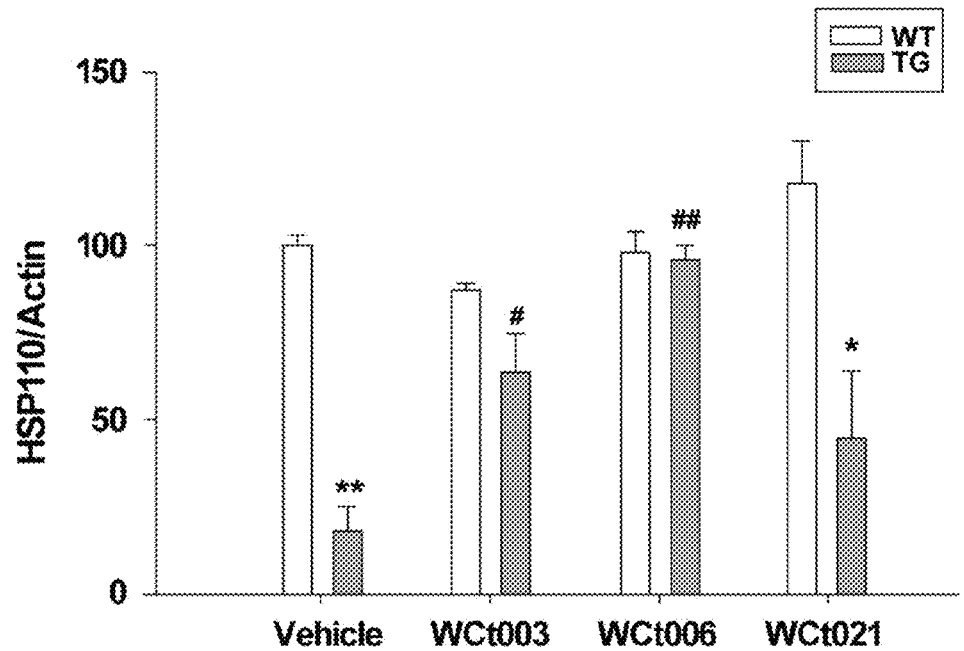
FIG. 13C is a bar chart illustrating the increase of chaperone HSP110 expression level after NiSOD-like compounds treatment according to an embodiment of the present invention.

J. NiSOD-like Compounds Treatment Increases Chaperone Expression in SCA17 Mouse Cerebellum Refer to FIG. 13A. Protein was extracted from the cerebellum of 14-week old mice and used to conduct the Western blot analysis of chaperones HSP40 and HSP110. Refer to FIGS. 13B and 13C. The quantitative result of Western blot shows the WCt003 and WCt006 compounds can significantly increase the expression of chaperones HSP40 and HSP 110. In FIGS. 13B and 13C, * and # indicate $p<0.05$; ** and ## indicate $p<0.01$; ### indicate $p<0.001$, wherein the * is TG vs. WT, and # is TG/WCt vs. TG/vehicle.

III. Experiments of Alzheimer's Disease (AD)

In the cell experiment models of AD, synthetic compounds WCt003, WCt006 and WCt021 were applied to demonstrate how WCt003, WCt006 and WCt021 are likely to work in suppressing the accumulation of abnormally folded Aβ oligomer and tau proteins and further increase the cell survival.

Figure 14:
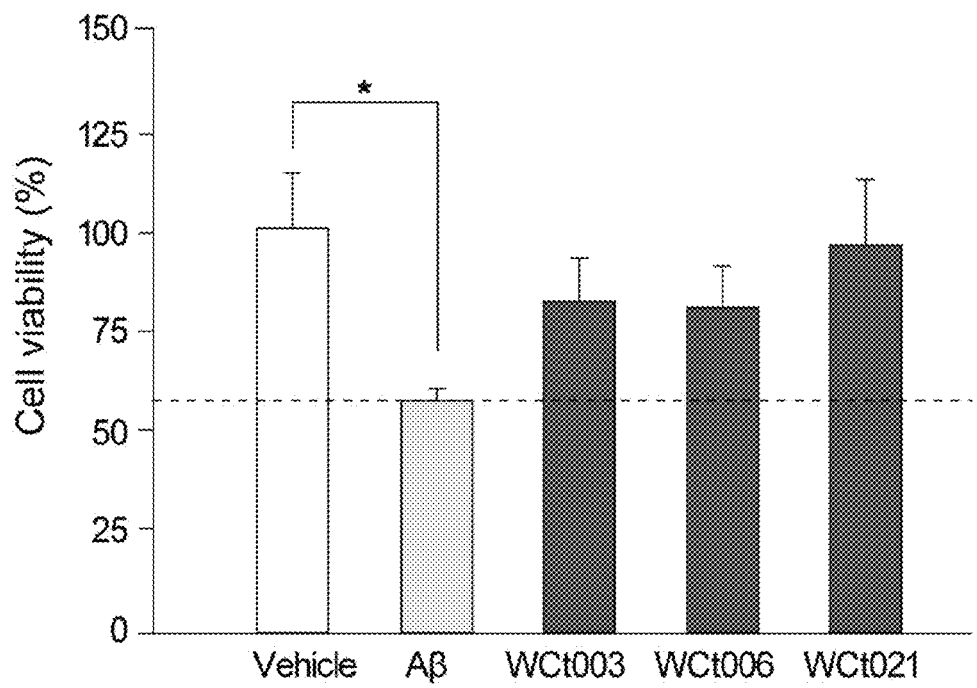
FIG. 14 is a bar chart illustrating the decrease of cell viability caused by the cytotoxicity of Aβ oligomer and the recovery of cell viability resulted from NiSOD-like compounds treatment according to an embodiment of the present invention.

A. Cell Viability Assay and NiSOD-Like Compounds Treatment Increases the Cell Survival, Mature Neuron Number and Neurite Outgrowth Length of AD Hippocampal Primary Culture Added with Aβ Oligomer For the Aβ oligomer experiment models, primary neurons were isolated from mouse hippocampus at embryonic day 16 to 18, and cultured on 48-well culture dishes. Thirty minutes before Aβ oligomer addition, NiSOD-like compounds were applied to the primary culture with the concentration of 0.25 μM, 0.5 μM and 1 μM. Primary cells were harvested for MTT cell viability assay and immunofluorescent staining after Aβ oligomer addition with concentration of 1 μM for 3 hours. Refer to FIG. 14. The cell viability was analyzed by MTT assay. Aβ oligomer induced cytotoxicity and reduced the cell viability, but NiSOD-like compounds treatment in concentration of 1 μM recovered the cell viability.

Figure 15:
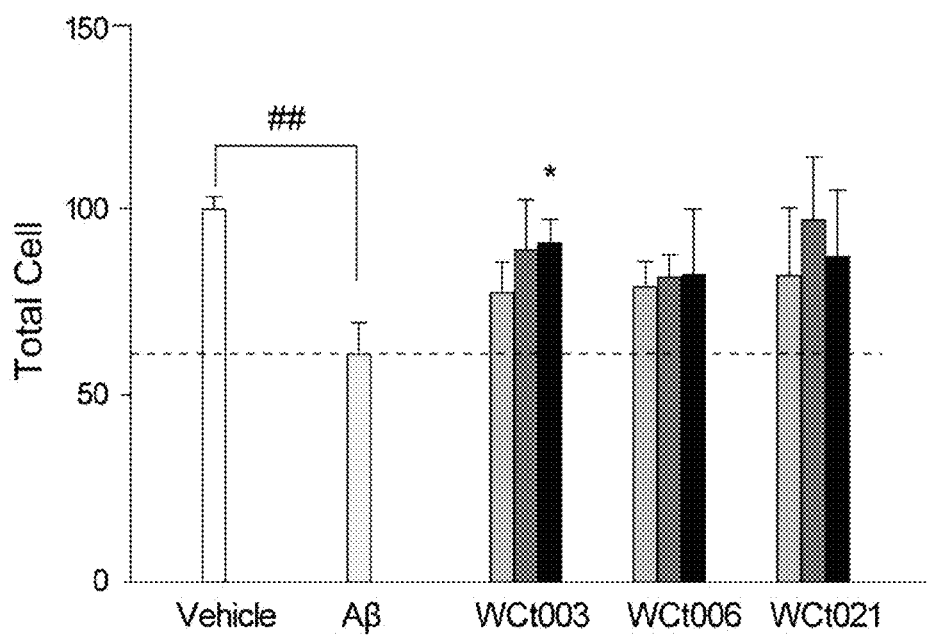
FIG. 15 is a bar chart illustrating the decrease of total cell survival caused by the cytotoxicity of Aβ oligomer and the recovery of total cell survival resulted from NiSOD-like compounds treatment according to an embodiment of the present invention.
Figure 16:
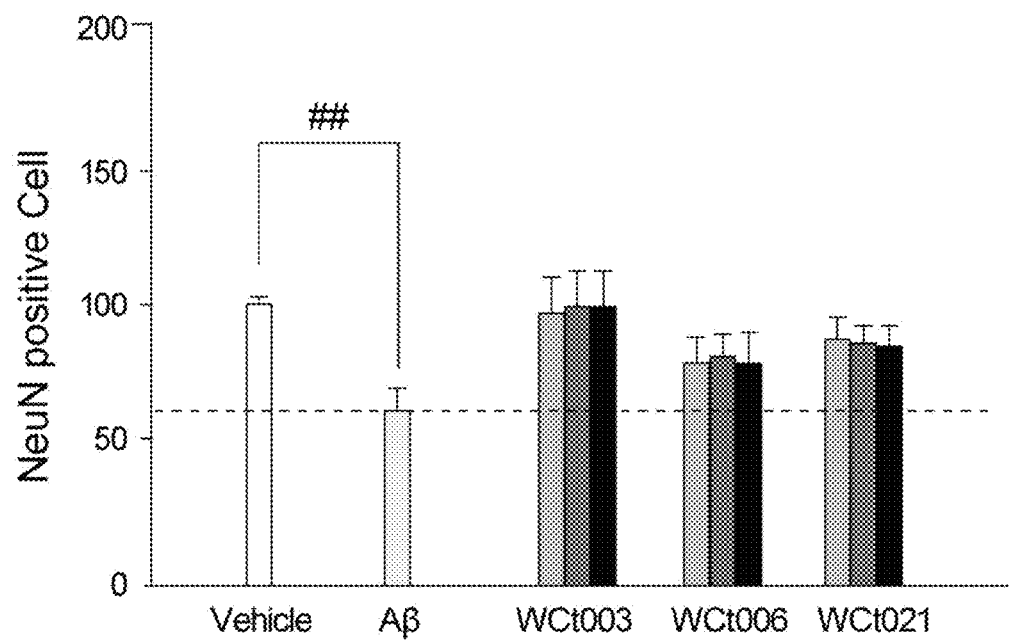
FIG. 16 is a bar chart illustrating the decrease of mature neuron number caused by the cytotoxicity of Aβ oligomer and the recovery of mature neuron number resulted from NiSOD-like compounds treatment according to an embodiment of the present invention.
Figure 17:
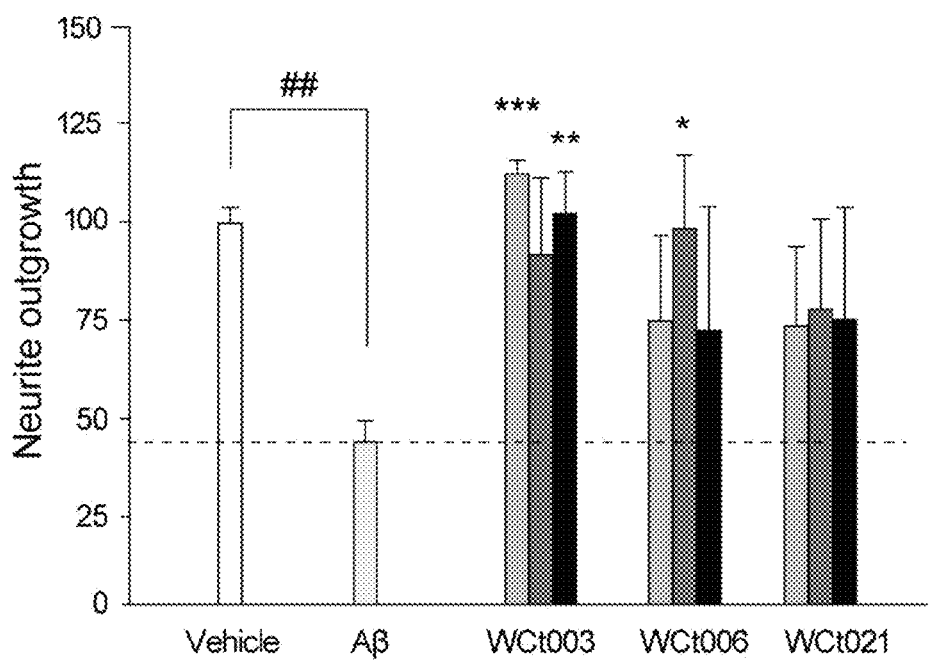
FIG. 17 is a bar chart illustrating the decrease of neurite outgrowth caused by the cytotoxicity of Aβ oligomer and the recovery of neurite outgrowth resulted from NiSOD-like compounds treatment according to an embodiment of the present invention.

Refer to FIGS. 15, 16 and 17. Immunofluorescent staining of primary cells with NeuN (mature neuron number) and MAP2 (neurite outgrowth) antibodies and nuclei DAPI staining (total cell number) shows Aβ oligomer cytotoxicity reduced the total cell, mature neurons and neurite outgrowth; while NiSOD-like compounds treatment can recover these phenotypes. In FIGS. 15, 16 and 17, * indicates $p<0.05$;  indicates $p<0.01$; * indicates $p<0.001$.

Figure 18:
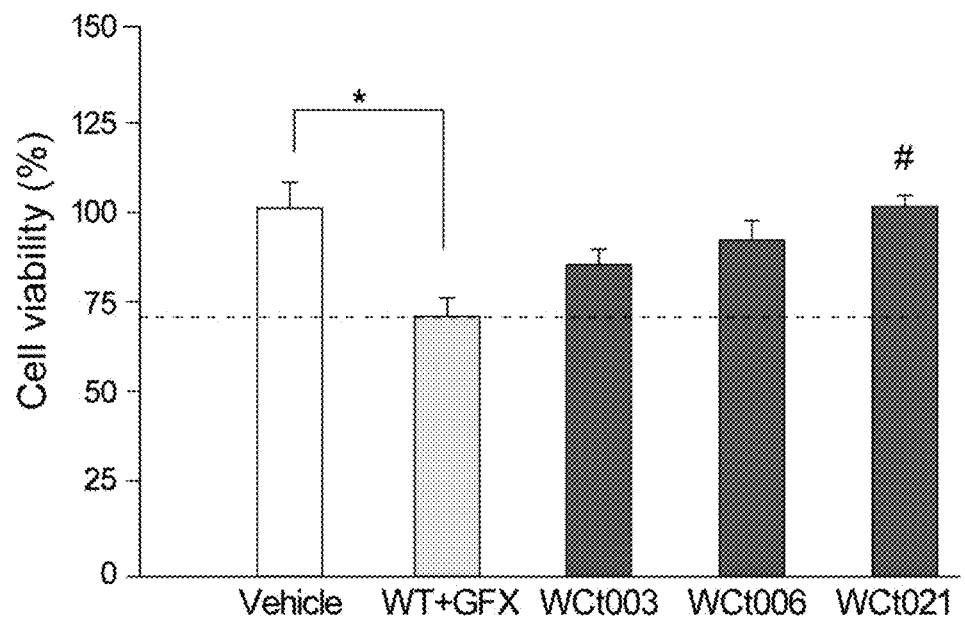
FIG. 18 is a bar chart illustrating the decrease of cell viability caused by the cytotoxicity of WT and GFX and the recovery of cell viability resulted from NiSOD-like compounds treatment according to an embodiment of the present invention.

B. Cell Viability Assay and NiSOD-Like Compounds Treatment Increases the Cell Survival, Mature Neuron Number and Neurite Outgrowth Length of AD Hippocampal Primary Culture Added with WT and GFX For tau proteins experiment models, primary neurons were isolated from mouse hippocampus at embryonic day 16 to 18, and cultured on 48-well culture dishes. Thirty minutes before WT (wortmannin, 10 μM) and GFX (GF-109203X, 10 μM) addition, NiSOD-like compounds were applied to the primary culture with the concentration of 0.25 µM, 0.5 µM and 1 µM. Primary cells were harvested for MTT cell viability assay and immunofluorescent staining after WT and GFX addition with concentration of 10 µM for 3 hours. Refer to FIG. 18. The cell viability was analyzed by MTT assay. WT and GFX induced cytotoxicity and reduced the cell viability, but NiSOD-like compounds treatment in concentration of 1 µM recovered the cell viability.

Figure 19:
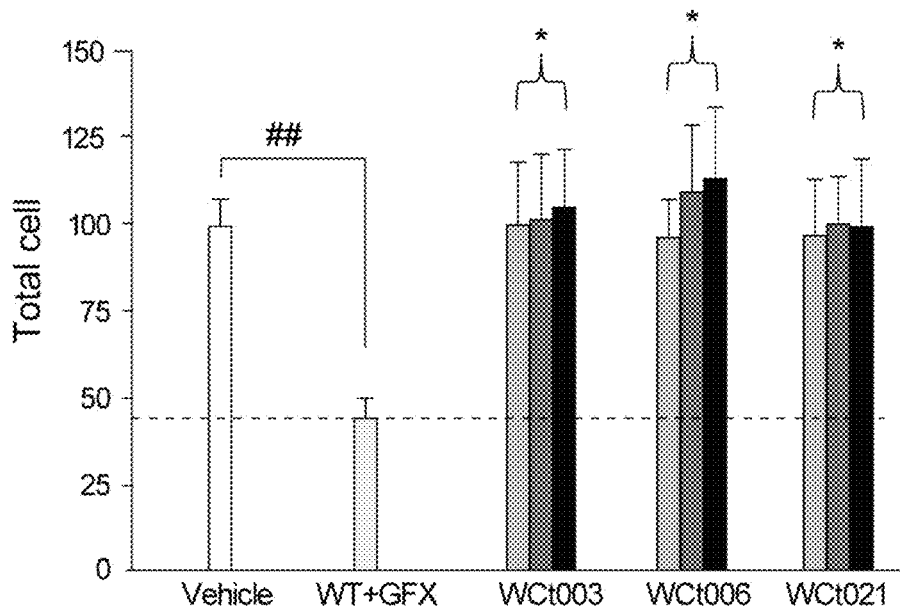
FIG. 19 is a bar chart illustrating the decrease of total cell survival caused by the cytotoxicity of WT and GFX and the recovery of total cell survival resulted from NiSOD-like compounds treatment according to an embodiment of the present invention.
Figure 20:
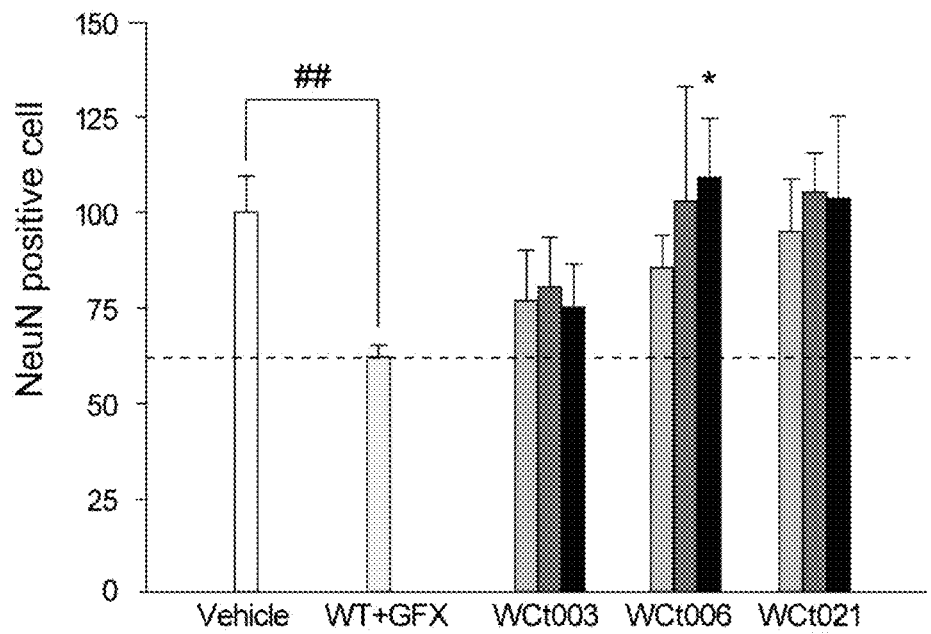
FIG. 20 is a bar chart illustrating the decrease of mature neuron number caused by the cytotoxicity of WT and GFX and the recovery of mature neuron number resulted from NiSOD-like compounds treatment according to an embodiment of the present invention.
Figure 21:
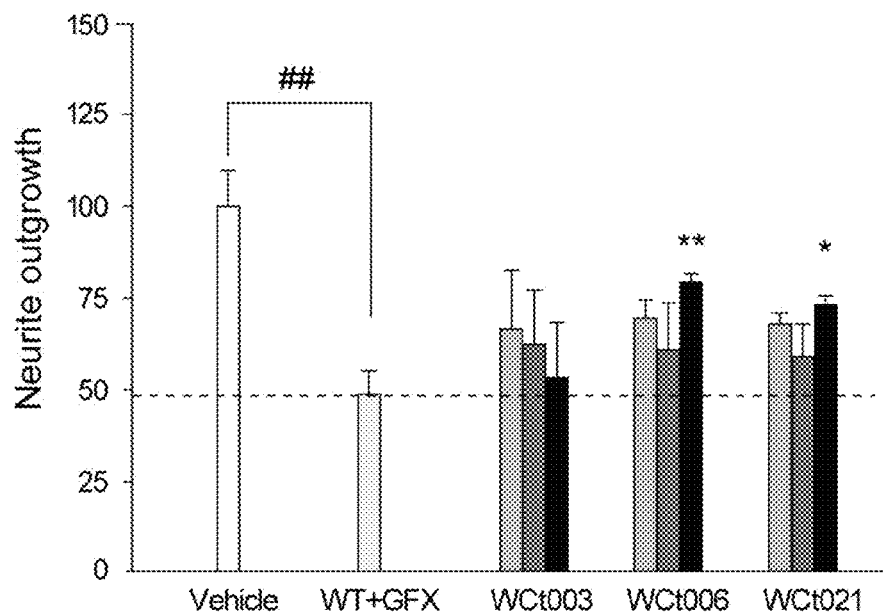
FIG. 21 is a bar chart illustrating the decrease of neurite outgrowth caused by the cytotoxicity of WT and GFX and the recovery of neurite outgrowth resulted from NiSOD-like compounds treatment according to an embodiment of the present invention.

Refer to FIGS. 19, 20 and 21. Immunofluorescent staining of primary cells with NeuN (mature neuron number) and MAP2 (neurite outgrowth) antibodies and nuclei DAPI staining (total cell number) show WT and GFX cytotoxicity reduced the total cell, mature neurons and neurite outgrowth; while NiSOD-like compounds treatment can recover these phenotypes. In FIGS. 19, 20 and 21, * and # indicate p<0.05; ** and ## indicate p<0.01.

IV. Experiments of Parkinson's Disease (PD)

In the cell and animal experiment models of PD, synthetic compounds WCt003, WCt006 and WCt021 were applied to demonstrate how WCt003, WCt006 and WCt021 are likely to work in protecting dopaminergic cells and reducing ROS production.

A. NiSOD-like Compound Reduces the 6-OHDA-Induced Apoptosis of PC12 Cells

Figure 22A:
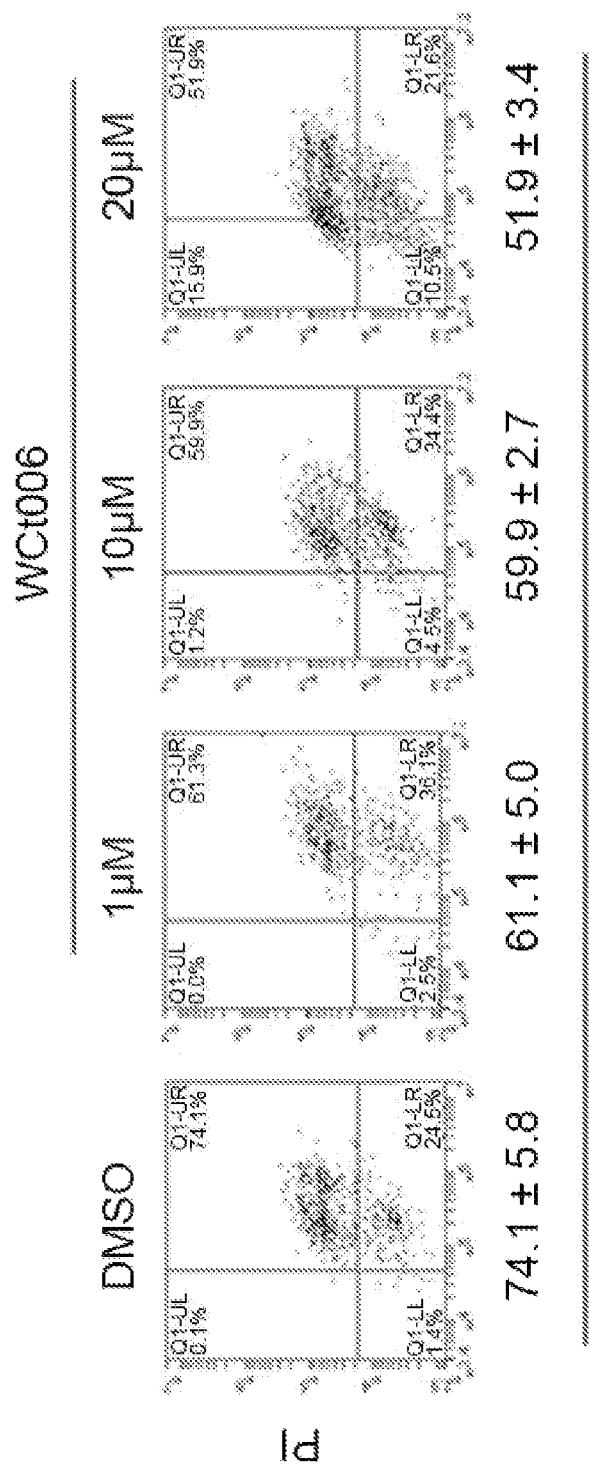
FIG. 22A shows flowcytometric assay images of the damage level of PC12 cells co-stained by PI and Annexin V with different concentrations of NiSOD-like compound according to an embodiment of the present invention.

PC 12 cells were treated with NiSOD-like compound, WCt006, with concentration of 1 µM, 10 µM and 20 µM for 5 minutes and then co-incubated with 50 µM of 6-OHDA (6-hydroxydopamine) for 24 hours. The 6-OHDA is not an ROS, but it can induce ROS causing damage to PC12 cells. Refer to FIG. 22A. PC12 cells were co-stained by PI and Annexin V for flowcytometric assay. The PI and Annexin V stain cell membrane protein when eversion of cell membrane occurs; therefore, the PI and Annexin V can be indexes for cell death. In FIG. 22A, it is noted that with the concentration of WCt006 increases the damage level decreases.

Figure 22B:
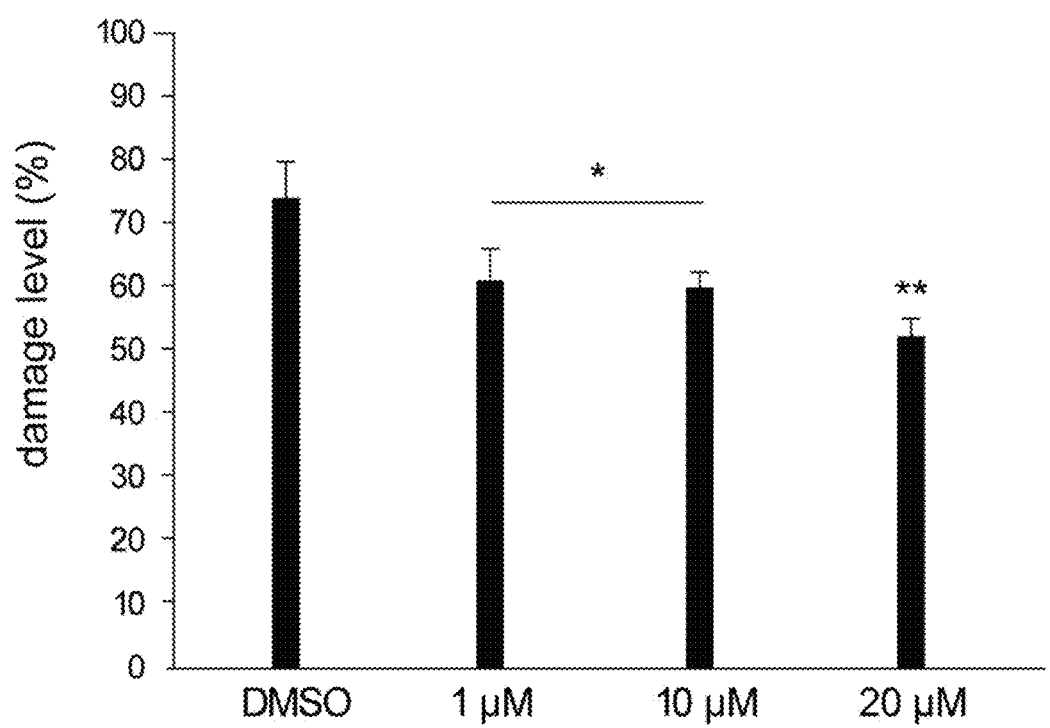
FIG. 22B is a bar chart illustrating the damage level of PC12 cells with different concentrations of NiSOD-like compound according to an embodiment of the present invention.

Refer to FIG. 22B. The data were shown as means±S.E. and compared to the control (DMSO). Statistical significance was analyzed by using Fisher's LSD. In FIG. 22B, * indicates p<0.05; ** indicates p<0.01.

Figure 23A:
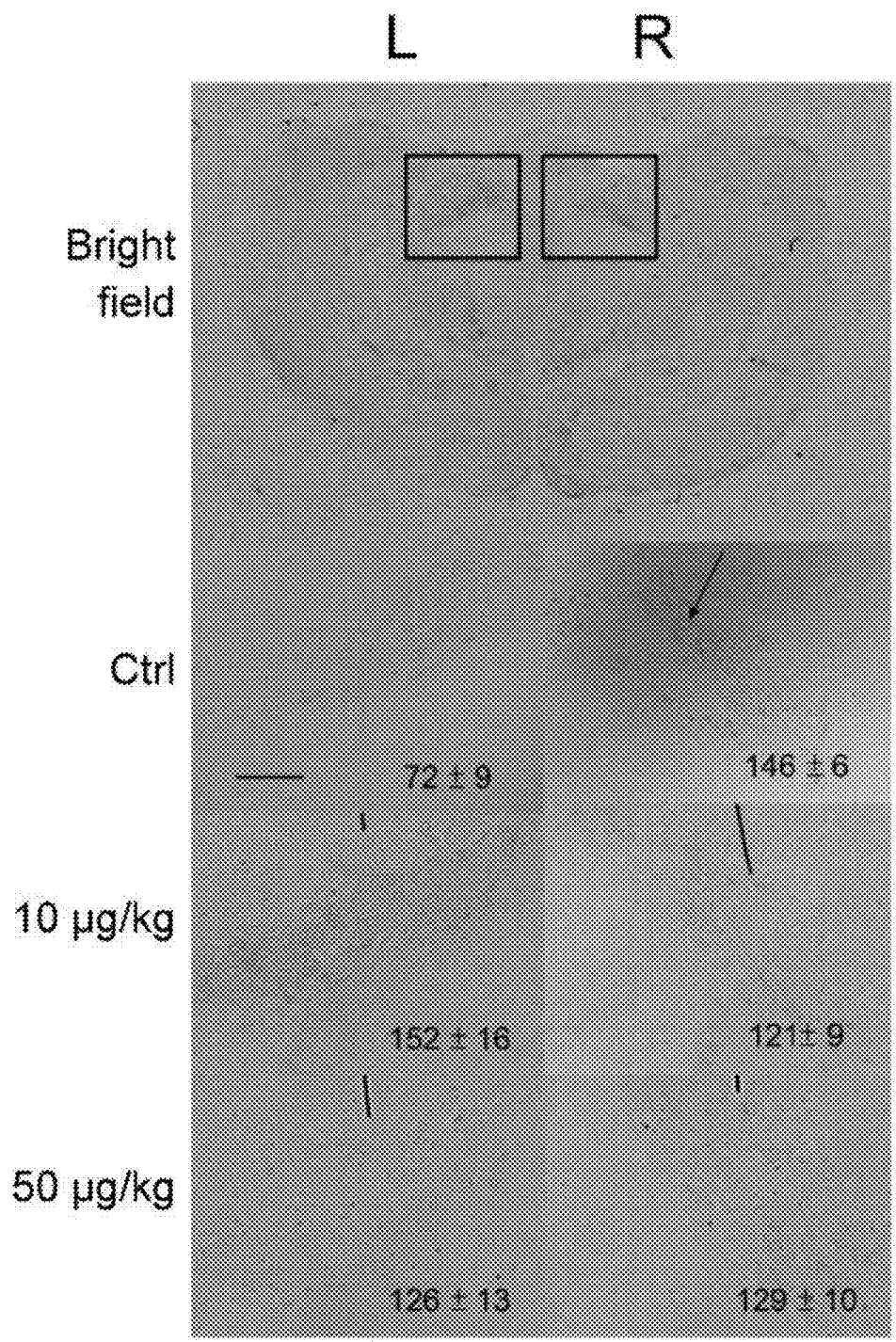
FIG. 23A is an immunostaining image showing the number of dopaminergic cells with the pre-treatment of NiSOD-like compound in comparison between left and right brain according to an embodiment of the present invention.

B. NiSOD-Like Compound Protects Dopaminergic Cells from 6-OHDA-Induced Injury 10-week-old rats were pre-injected with 10 µg/kg and 50 µg/kg of NiSOD-like compound, WCt006, for 2 weeks and then treated with 6-OHDA (2 mg/ml) in the left brain. Refer to FIG. 23A. The slices were immunostained by mouse anti-tyrosine hydroxylase (TH, 1:2500) antibody which is used specifically for dopaminergic cells. The substantia nigra on the brain slice was squared. The dopaminergic cells were indicated as arrow head and the numbers of these cells were shown on the panels from three repeats. Bar=50 µm. In FIG. 23A, it is noted that with the pre-treatment of WCt006, the numbers of dopaminergic cells in both of left and right brains were similar.

Figure 23B:
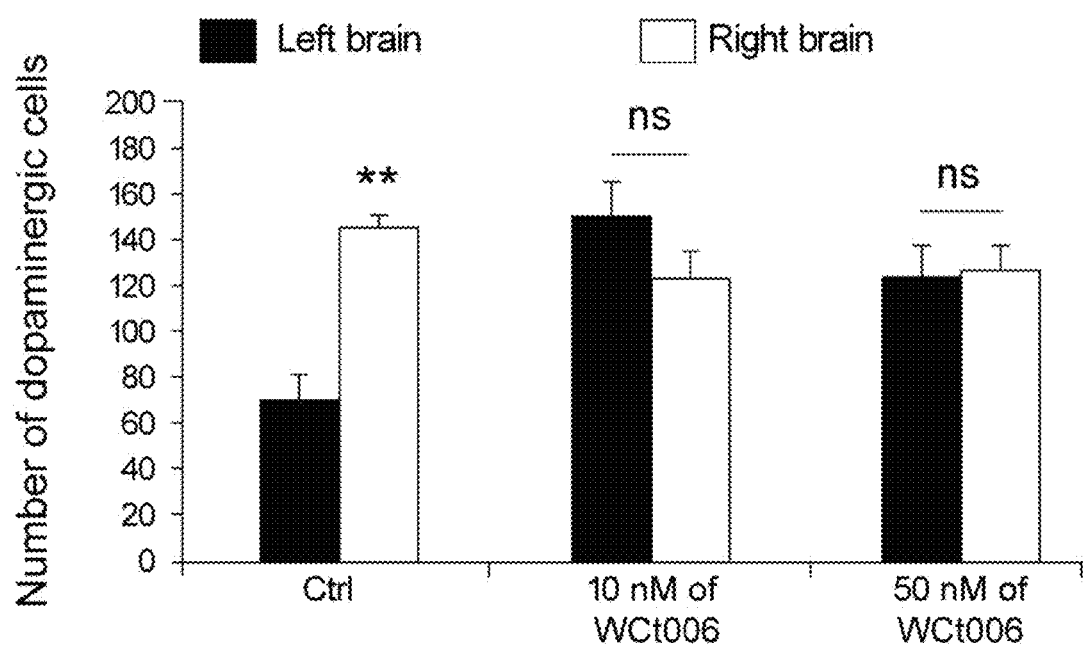
FIG. 23B is a bar chart illustrating the number of dopaminergic cells with the pre-treatment of NiSOD-like compound in comparison between left and right brain according to an embodiment of the present invention.

Refer to 23B. The data of left and right brain were shown as means±S.E. Statistical significance between left and right brain was analyzed by using Fisher's LSD. In FIG. 23B, ** indicates p<0.01; ns indicates no significance.

Figure 24A:
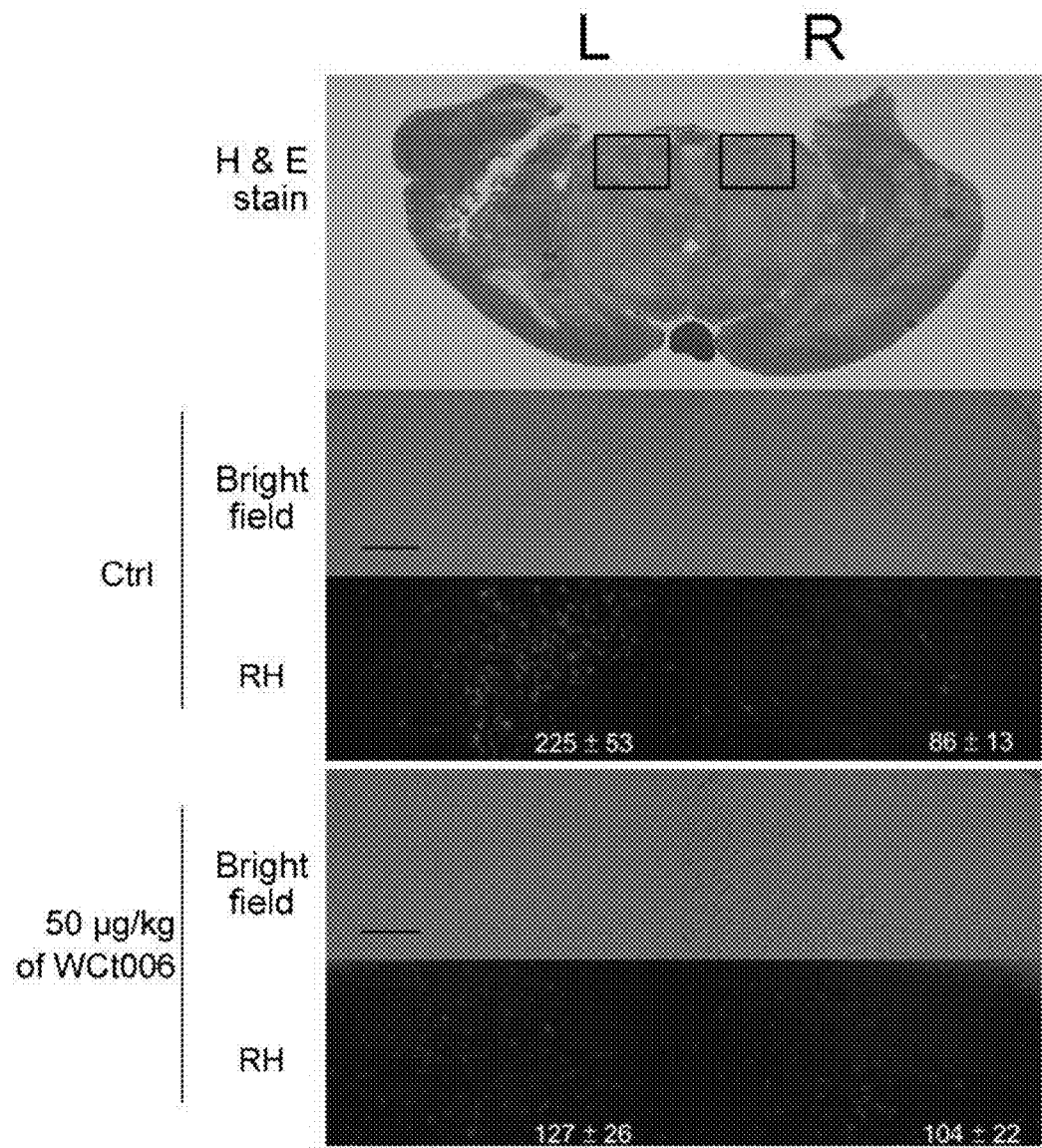
FIG. 24A is a fluorescence microscopy image showing the production of nitric oxide with the pre-treatment of NiSOD-like compound in comparison between left and right brain according to an embodiment of the present invention.

C. NiSOD-Like Compound Attenuates the Production of Nitric Oxide Under the Stress of 6-OHDA 10-week-old rats were pre-injected with 50 µg/kg of NiSOD-like compound, WCt006, for 2 weeks and then treated with 6-OHDA (2 mg/ml) in the left brain. Refer to FIG. 24A. The 2.38 mg/kg of RH nitric oxide probe was injected by intraperitoneal injection for 30 minutes and the brain slices were observed by fluorescent microscope. The neuron cells with increased nitric oxide were counted and shown in the panel from three repeats. The slice of whole brain was stained by H&E. Bar=50 µm. In FIG. 24A, it is noted that with the pre-treatment of WCt006, the production of nitric oxide decreases, which implies the dopaminergic cells can be protected from the damage of nitric oxide as an ROS.

Figure 24B:
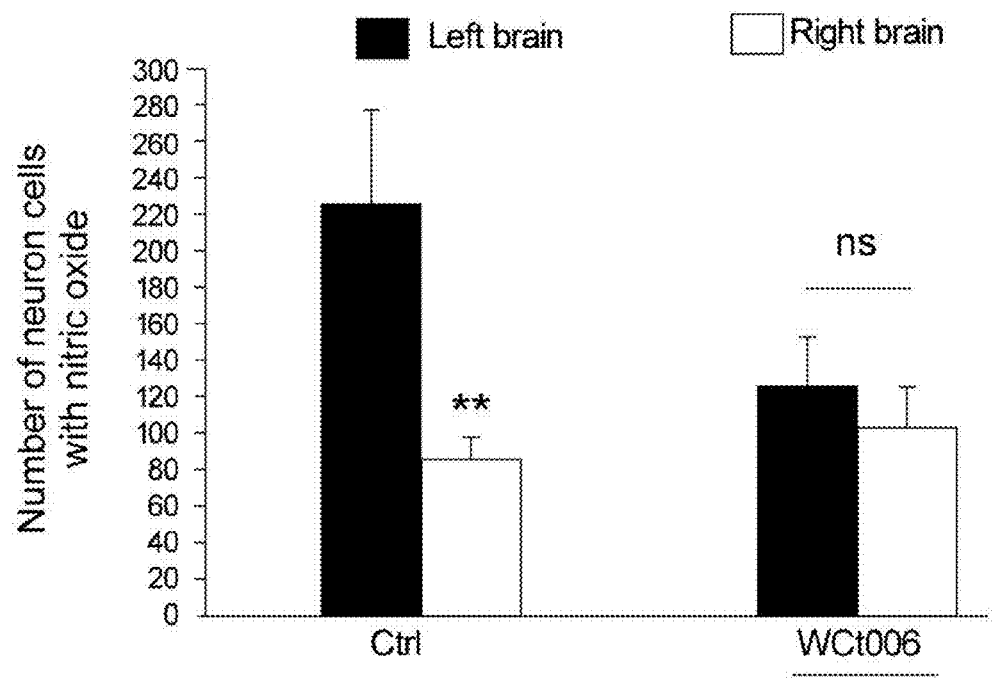
FIG. 24B is a bar chart illustrating the production of nitric oxide with the pre-treatment of NiSOD-like compound in comparison between left and right brain according to an embodiment of the present invention.

Refer to FIG. 24B. The data of left and right brain were shown as means±S.E. Statistical significance between left and right brain was analyzed by using Fisher's LSD. In FIG. 24B, ** indicates p<0.01; ns indicates no significance.

D. NiSOD-Like Compound Reduces Ipsiversive Rotation Caused by 6-OHDA

Figure 25:
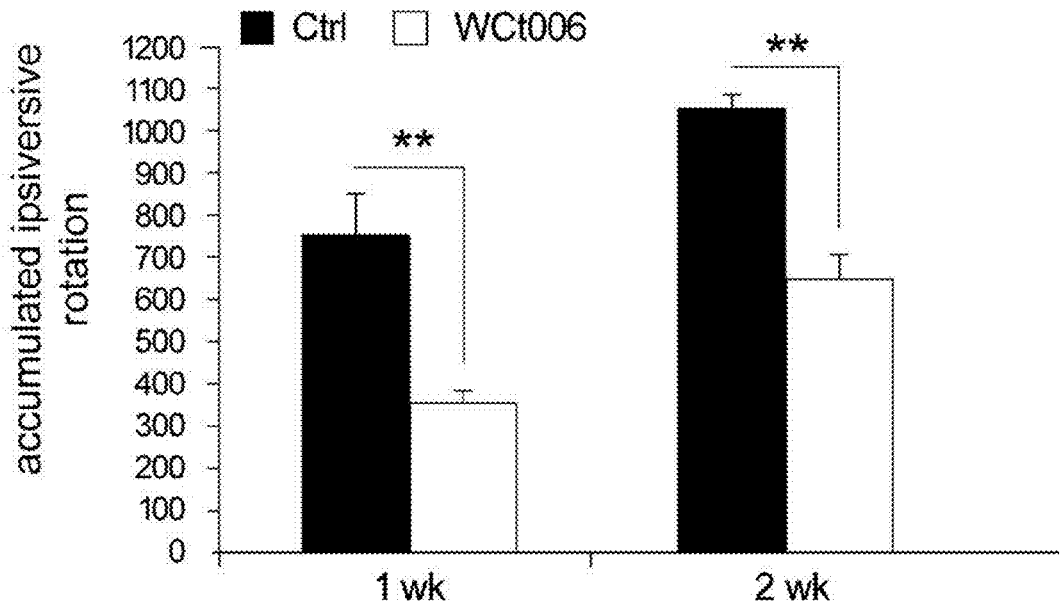
FIG. 25 is a bar chart illustrating the observation of ipsi-versive rotation for two weeks in comparison with untreated of NiSOD-like compound and pretreated of NiSOD-like compound according to an embodiment of the present invention.

After damaged by 6-OHDA, the apomophine (0.75 mg apomophine and 0.2% Vitamine C dissolved in 1 ml saline) which stimulates ipsiversive rotation was intraperitoneal injected to the rats either with or without the treatment of WCt006. Refer to FIG. 25. The accumulated rotations of each treatment were statistically calculated. In FIG. 25, n=6; ** indicates p<0.01.

The experiments and results presented above in the present invention demonstrate that the NiSOD-like compounds suppress abnormal protein aggregation, recover cell viability, increase mature neuron number and neurite outgrowth length and protect dopaminergic cells by reducing oxidative stress or reactive oxygen species in brain tissues. The present invention may be applied to other neurodegenerative disorders with similar pathogenic mechanism as well. The present invention utilizes the NiSOD-like compound or its derivatives suppressing abnormal protein aggregation, recovering cell viability, increasing mature neuron number and neurite outgrowth length and protecting dopaminergic cells by reducing oxidative stress or reactive oxygen species in brain tissues in neurodegenerative disorders including spinocerebellar ataxia, Alzheimer's disease or Parkinson's disease, and provides the effective dose according to the experiments and results presented above in a concentration between 1 nM to 4 µM (0.5 µg/kg to 2 mg/kg).

The foregoing embodiments are illustrative of the characteristics of the present invention so as to enable a person skilled in the art to understand the disclosed subject matter and implement the present invention accordingly. The embodiments, however, are not intended to restrict the scope of the present invention. Hence, all equivalent modifications and variations made in the foregoing embodiments without departing from the spirit and principle of the present invention should fall within the scope of the appended claims.

What is claimed is:

1. A NiSOD-like compound ($[NiH_2BDPP(L)]^{2+}$) or derivatives thereof represented by structural formulas as follows:

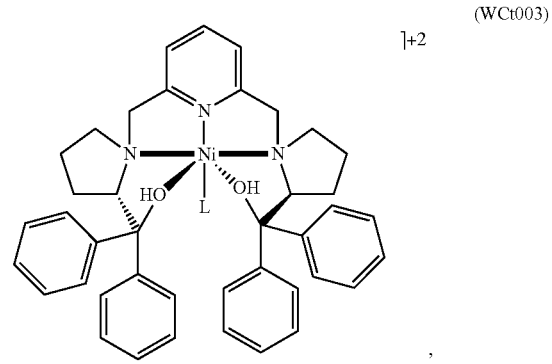

(WCt003)

-continued

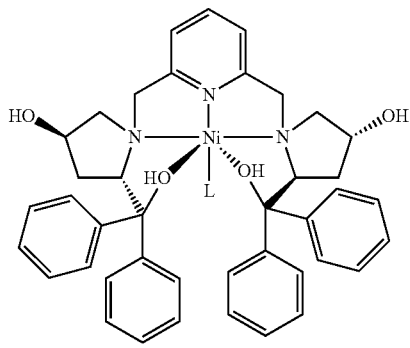
(WCt006)

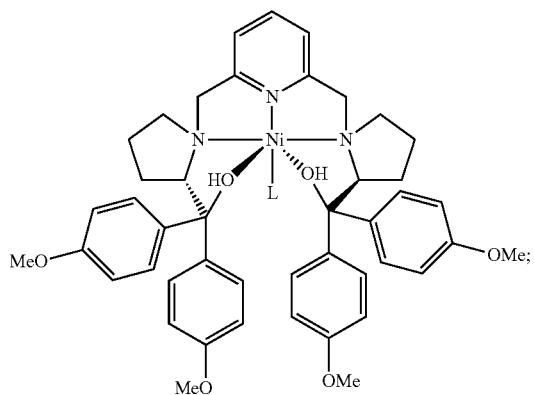
(WCt021)

L is acetonitrile, water or tert-butyl isocyanate;
wherein the NiSOD-like compound or derivatives thereof suppress abnormal protein aggregation, recover cell viability, increase mature neuron number and neurite outgrowth length and protect dopaminergic cells by reducing oxidative stress or reactive oxygen species (ROS) in brain tissues.

2. The NiSOD-like compound ($[NiH_2BDPP(L)]^{2+}$) or derivatives thereof according to claim 1, wherein the NiSOD-like compound or derivatives thereof suppress abnormal protein aggregation by reducing oxidative stress or ROS in brain tissues in spinocerebellar ataxia, Alzheimer's disease or Parkinson's disease.

3. The NiSOD-like compound ($[NiH_2BDPP(L)]^{2+}$) or derivatives thereof according to claim 2, wherein the an effective dose for suppressing abnormal protein aggregation by reducing oxidative stress or ROS in brain tissues is in a concentration between 1 nM to 4 μM (0.5 μg/kg to 2 mg/kg).

4. The NiSOD-like compound ($[NiH_2BDPP(L)]^{2+}$) or derivatives thereof according to claim 2, wherein the NiSOD-like compound or derivatives thereof improve movement performance in the spinocerebellar ataxia.

5. The NiSOD-like compound ($[NiH_2BDPP(L)]^{2+}$) or derivatives thereof according to claim 2, wherein the NiSOD-like compound or derivatives thereof increase glutathione level in the spinocerebellar ataxia.

6. The NiSOD-like compound ($[NiH_2BDPP(L)]^{2+}$) or derivatives thereof according to claim 2, wherein the NiSOD-like compound or derivatives thereof increase level of anti-oxidative enzymes in the spinocerebellar ataxia.

7. The NiSOD-like compound ($[NiH_2BDPP(L)]^{2+}$) or derivatives thereof according to claim 2, wherein the NiSOD-like compound or derivatives thereof increase chaperone expression in the spinocerebellar ataxia.

8. The NiSOD-like compound ($[NiH_2BDPP(L)]^{2+}$) or derivatives thereof according to claim 2, wherein the NiSOD-like compound or derivatives thereof recover cell viability and increase mature neuron number and neurite outgrowth length in the Alzheimer's disease.

9. The NiSOD-like compound ($[NiH_2BDPP(L)]^{2+}$) or derivatives thereof according to claim 2, wherein the NiSOD-like compound or derivatives thereof protect dopaminergic cells from damage of 6-OHDA (6-hydroxydopamine) induced nitric oxide production in the Parkinson's disease.

10. The NiSOD-like compound ($[NiH_2BDPP(L)]^{2+}$) or derivatives thereof according to claim 2, wherein the NiSOD-like compound or derivatives thereof improve movement performance by reducing ipsiversive rotation in the Parkinson's disease.

* * * * *